US012071614B2

(12) United States Patent
Laffend et al.

(10) Patent No.: US 12,071,614 B2
(45) Date of Patent: Aug. 27, 2024

(54) INCREASING ACTIVITY OF 2'FUCOSYLLACTOSE TRANSPORTERS ENDOGENOUS TO MICROBIAL CELLS

(71) Applicant: INBIOSE N.V., Zwijnaarde (BE)

(72) Inventors: Lisa A. Laffend, Claymont, DE (US); Mark J. Nelson, Newark, DE (US); Lori Ann Maggio-Hall, Wilmington, DE (US)

(73) Assignee: INBIOSE N.V., Zwijnaarde (BE)

( * ) Notice: Subject to any disclaimer, the term of this patent is extended or adjusted under 35 U.S.C. 154(b) by 0 days.

(21) Appl. No.: 17/049,855

(22) PCT Filed: Apr. 23, 2018

(86) PCT No.: PCT/US2018/028842
§ 371 (c)(1),
(2) Date: Oct. 22, 2020

(87) PCT Pub. No.: WO2019/209245
PCT Pub. Date: Oct. 31, 2019

(65) Prior Publication Data
US 2021/0071134 A1    Mar. 11, 2021

(51) Int. Cl.
*C12N 1/38* (2006.01)
*C12N 1/18* (2006.01)
*C12P 19/18* (2006.01)

(52) U.S. Cl.
CPC .................. *C12N 1/38* (2013.01); *C12N 1/18* (2013.01); *C12P 19/18* (2013.01)

(58) Field of Classification Search
CPC .............. C12N 1/38; C12N 1/18; C12P 19/18
See application file for complete search history.

(56) References Cited

U.S. PATENT DOCUMENTS

| 7,932,063 B2 | 4/2011 | Dunson, Jr. et al. |
| 8,652,808 B2 | 2/2014 | Jennewein et al. |
| 8,871,488 B2 | 10/2014 | Dauner et al. |
| 2010/0120701 A1 | 5/2010 | McCoy et al. |
| 2013/0203138 A1 | 8/2013 | McElvain et al. |
| 2013/0252296 A1 | 9/2013 | Maggio-Hall |
| 2014/0024820 A1 | 1/2014 | Parkot et al. |
| 2017/0152538 A1* | 6/2017 | Lee .................... C12P 19/18 431/237 |

FOREIGN PATENT DOCUMENTS

| EP | 2927316 A1 | 10/2015 |
| WO | 2010/142305 A1 | 12/2010 |
| WO | 2011/038019 A2 | 3/2011 |
| WO | 2014/151645 A1 | 9/2014 |
| WO | 2015/032412 A1 | 3/2015 |
| WO | 2016/075243 A1 | 5/2016 |
| WO | 2017/042382 A1 | 3/2017 |

OTHER PUBLICATIONS

Lim, Hayoon, Metabolic engineering of *Saccharomyces cerevisiae* for efficient production of 2'-fucosyllactose, 2017, College of Liberal Arts and Sciences University of Illinois Urbana-Champaign, Illinois Dissertation, (Year: 2017).*
Lim, H. (2017). Metabolic engineering of *Saccharomyces cerevisiae* for efficient production of 2'-fucosyllactose, Thesis (Year: 2017).*
Boos, Winfried, and Howard Shuman. "Maltose/maltodextrin system of *Escherichia coli*: transport, metabolism, and regulation." Microbiology and Molecular Biology Reviews 62.1 (1998): 204-229. (Year: 1998).*
Chin et al: "Metabolic engineering of *Escherichia coli* to produce 2'-fucosyllactose via salvage pathway of guanosine 5'-diphosphate (GDP)-L-fucose", Biotechnology and Bioengineering,, vol. 113, Jun. 20, 2016 (Jun. 20, 2016), pp. 2443-2452, XP002765455.
International Search Report for International Application No. PCT/US18/28842, mailed Feb. 5, 2019, 9 pages.
International Written Opinion for International Application No. PCT/US18/28842, mailed Feb. 5, 2019, 11 pages.
Jennewein: "Abschlussbericht zum Forderprojekt Entwicklung eines innovativen Produktionsverfahrens fUr Fucosyllctosen Mit dem Forderkennzeichen: BMBF Projekt 0315170", Internet Citation, Jan. 1, 2012 (Jan. 1, 2012), pp. 1-31, XP002753121.
Petschacher Barbara et al: "Biotechnological production of fucosylated human milk oligosaccharides: Prokaryotic fucosyltransferases and their use in biocatalytic cascades or whole cell conversion systems", Journal of Biotechnology, Elsevier, Amsterdam, NL, vol. 235, Apr. 1, 2016 (Apr. 1, 2016), pp. 61-83, XP029733274.
Hollands et al. "Engineering two species of yeast as cell factories for 2'-fucosyllactose" Metabolic Engineering, 52, 232-242 (2019).
Chin et al. "Metabolic engineering of Corynebacterium glutamicum to produce GDP-L-fucose from glucose and mannose" Bioprocess Biosyst. Eng., (2013), vol. 36, pp. 749-756.
Lee et al., "Whole cell biosynthesis of a functional oligosaccharide, 2'0-fucosyllactose, using engineered *Escherichia coli*" Microb. Cell Factories, (2012), vol. 11, pp. 48-57.
Mattila et al."Functional expression of *Escherichia coli* enzymes synthesizing GDP-L-fucose from inherent GDP-D-mannose in *Saccharomyces cerevisiae*" Glycobiology, (2000), vol. 10, pp. 1041-1047.
Sherman, "Getting started with yeast", Methods in Enzymology, (2002), vol. 350, pp. 3-41.

* cited by examiner

*Primary Examiner* — Robert J Yamasaki
*Assistant Examiner* — Trevor Kane
(74) *Attorney, Agent, or Firm* — TraskBritt

(57) ABSTRACT

A fermentation broth which includes a microbial cell which has been subjected to a condition under which the activity an endogenous transporter for 2' fucosyllactose is increased. Also provided are methods for increasing export of 2' fucosyllactose from a microbial cell, methods for identifying an endogenous yeast transporter of 2' fucosyllactose, and microbial cells genetically engineered to increase the activity of an endogenous transporter of 2' fucosyllactose.

3 Claims, 10 Drawing Sheets
Specification includes a Sequence Listing.

SEQUENCE LISTING

```
<160> NUMBER OF SEQ ID NOS: 46

<210> SEQ ID NO 1
<211> LENGTH: 1764
<212> TYPE: DNA
<213> ORGANISM: Kluyveromyces lactis

<400> SEQUENCE: 1
atggccgacc actcaagttc cagctcttct ttgcaaaaga aaccaatcaa caccatcgaa      60
cacaaggata ctttgggaaa cgacagagat cacaaggaag ccttgaactc cgacaacgac     120
aatacttctg gcttgaagat taacggtgtt ccaatcgagg atgccagaga agaagtcttg     180
ttacctggtt acctatccaa gcaatactac aaattgtacg gtttatgttt catcacttac     240
ttgtgtgcta ccatgcaagg atacgatggt gctttgatgg gctctatcta caccgaagac     300
gcttacttaa agtactacca cttggatatc aactccagtt ctggtaccgg cttggttttc     360
tccattttca acgttggtca aatctgtgga gctttctttg tcccattgat ggactggaag     420
ggcagaaaac cagctatcct aattggttgt ttgggcgttg tcattggtgc tatcatcagt     480
tctttgacta caaccaagtc tgctttgatc ggtggcagat ggtttgttgc tttcttcgcc     540
actattgcca acgctgccgc tccaacttac tgtgccgaag ttgctccagc tcacttgcgt     600
ggcaaggttg ctggtttgta caacaccttg tggtccgtcg gttctattgt tgctgccttc     660
tctacttacg gtaccaacaa gaatttccca aactcttcca aggctttcaa aatcccttg      720 tacttacaaa tgatgttccc aggtttggtt tgcattttcg gttggttgat cccagaatct     780
cccagatggt tggtcggtgt tggaagggag gaagaagcca gagagttcat cattaagtac     840
cacttgaacg gcgacagaac ccacccattg ctggacatgg agatggccga aatcattgag     900
tctttccacg gtaccgactt gtccaaccca ctggaaatgt tggacgttcg ttctctattc     960
agaaccaggt ccgaccgtta cagagctatg ttggtcatct taatggcctg gtttggtcaa    1020
ttctctggaa acaatgtttg ttcttactac ttaccaacta tgttgagaaa cgttggtatg    1080
aagtccgtct ctctaaacgt attgatgaat ggtgtctact ctatcgttac ctggatatct    1140
tccatttgtg gtgctttctt tatcgacaag attggcagga gagaaggttt cttgggctcc    1200
atctctggtg ctgccttggc tttaactggt ctatctatct gtactgccag atacgaaaag    1260
accaagaaaa agtctgcctc caacggtgct ttggttttca tctacctatt tggtggaatc    1320
ttctcttttg ctttcactcc aatgcaatct atgtactcca ccgaagtctc tacaaacttg    1380
accagatcaa aggctcaatt gttaaacttc gttgtctctg gtgtggctca attcgtcaac    1440
caatttgcca ctccaaaggc tatgaaaaac atcaagtact ggttttacgt tttctacgtc    1500
```
ttctttgaca tcttcgagtt cattgtcatc tactttttct tcgtcgaaac caagggcaga    1560
tccctggaag aattggaggt tgtcttcgaa gctccaaacc cgagaaaggc ttctgtcgat    1620
caagccttct tggctcaagt cagagccact ttggttcaaa gaaacgacgt ccgtgttgcc    1680
aatgctcaaa acttgaagga gcaagaacca ttgaagtccg acgccgatca tgtcgaaaag    1740
ttgtccgagg ccgaatctgt ttag                                          1764

<210> SEQ ID NO 2
<211> LENGTH: 30
<212> TYPE: DNA
<213> ORGANISM: artificial sequence
<220> FEATURE:
<223> OTHER INFORMATION: H89 primer

<400> SEQUENCE: 2
ctaaacagat tcggcctcgg acaacttttc                                      30

<210> SEQ ID NO 3
<211> LENGTH: 60
<212> TYPE: DNA
<213> ORGANISM: artificial sequence
<220> FEATURE:
<223> OTHER INFORMATION: H94 primer

<400> SEQUENCE: 3
agaaagattt aattatcaaa caatatcaat atggccgacc actcaagttc cagctcttct     60

<210> SEQ ID NO 4
<211> LENGTH: 470
<212> TYPE: DNA
<213> ORGANISM: Saccharomyces cerevisiae

<400> SEQUENCE: 4
tttttacctc tgtggaaatt gttactctca cactctttag ttcgtttgtt tgttttgttt     60
attccaatta tgaccggtga cgaaacgtgg tcgatggtgg gtaccgctta tgctcccctc    120
cattagtttc gattatataa aaaggccaaa tattgtatta ttttcaaatg tcctatcatt    180
atcgtctaac atcaatttc tcttaaattt tttctctttc tttcctataa caccaatagt    240
gaaaatcttt ttttcttcta tatctacaaa aactttttt ttctatcaac ctcgttgata    300 aatttttct ttaacaatcg ttaataatta attaattgga aaataaccat ttttctctc    360 ttttatacac acattcaaaa gaaagaaaaa aaatataccc cagctagtta agaaaatca    420 ttgaaaagaa taagaagata agaaagattt aattatcaaa caatatcaat               470

<210> SEQ ID NO 5
<211> LENGTH: 42
<212> TYPE: DNA
<213> ORGANISM: artificial sequence
<220> FEATURE:
<223> OTHER INFORMATION: H92 primer

<400> SEQUENCE: 5
gcaaaggatc cttttacct ctgtggaaat tgttactctc ac                        42

<210> SEQ ID NO 6
<211> LENGTH: 30
<212> TYPE: DNA
<213> ORGANISM: artificial sequence
<220> FEATURE:
<223> OTHER INFORMATION: H93 primer -continued

<400> SEQUENCE: 6
attgatattg tttgataatt aaatctttct                                      30

<210> SEQ ID NO 7
<211> LENGTH: 250
<212> TYPE: DNA
<213> ORGANISM: Saccharomyces cerevisiae

<400> SEQUENCE: 7
tgaacccgat gcaaatgaga cgatcgtcta ttcctggtcc ggttttctct gccctctctt    60
ctattcactt tttttatact ttatataaaa ttatataaat gacataactg aaacgccaca   120
cgtcctctcc tattcgttaa cgcctgtctg tagcgctgtt actgaagctg cgcaagtagt   180 ttttcaccg tataggccct cttttctct ctctttcttt ctctcccgcg ctgatctctt     240
cttcgaaaca                                                          250

<210> SEQ ID NO 8
<211> LENGTH: 60
<212> TYPE: DNA
<213> ORGANISM: artificial sequence
<220> FEATURE:
<223> OTHER INFORMATION: H90 primer

<400> SEQUENCE: 8
gaaaagttgt ccgaggccga atctgtttag tgaacccgat gcaaatgaga cgatcgtcta    60

<210> SEQ ID NO 9
<211> LENGTH: 44
<212> TYPE: DNA
<213> ORGANISM: artificial sequence
<220> FEATURE:
<223> OTHER INFORMATION: H91 primer

<400> SEQUENCE: 9
tccattgttt aaactgtttc gaagaagaga tcagcgcggg agag                     44

<210> SEQ ID NO 10
<211> LENGTH: 4827
<212> TYPE: DNA
<213> ORGANISM: artificial sequence
<220> FEATURE:
<223> OTHER INFORMATION: pUC19-URA3-YPRC plasmid

<400> SEQUENCE: 10
tcgcgcgttt cggtgatgac ggtgaaaacc tctgacacat gcagctcccg gagacggtca    60
cagcttgtct gtaagcggat gccggagca gacaagcccg tcagggcgcg tcagcgggtg   120
ttggcgggtg tcggggctgg cttaactatg cggcatcaga gcagattgta ctgagagtgc   180
accatatgcg gtgtgaaata ccgcacagat gcgtaaggag aaaataccgc atcaggcgcc   240
attcgccatt caggctgcgc aactgttggg aagggcgatc ggtgcgggcc tcttcgctat   300
tacgccagct ggcgaaaggg ggatgtgctg caaggcgatt aagttgggta acgccagggt   360
tttcccagtc acgacgttgt aaaacgacgg ccagtgaatt cgagctcggt accccaaaag   420
gaatattggg tcagatgaat ggacgcgaat gcaagacaga agtccaaatc acgtcaagac   480
aaagaaagaa agaaagaaaa actaacacat taatgtagtt ttaaatttc aaatccgaac    540 aacagagcat agggtttcgc aaaggatccg gcgcgccgtt taaacaatgg aaggtcggga   600
tgagcatata caagcactaa gaagaacaat acagaactct acacggtatt attgtgctac   660
aagctcgagt aaaaccgagt gttttgacga tactaacgtt gttaagaaag taacttgtta   720

```
tcaaactcat taccaacttg tgattaattg gtgaataata tgataattgt cgaaattcca      780
ttgttggtaa agcctataat attatgtata cagattatac tagaaattct ctcgagaata      840
taagaatccc caaaattgaa tcggtatttc tacatactaa tattaccatt acttctcctt     900
tcgttttata tgtttcattc ctattacatt atcgatcttt gcatttcagc ttccattata      960
tttgatgtct gttttatgtc cccacgttac accgcatgtg acagtatact agtaacatga     1020
gtgctaccga atagatgaca ttttagactt tcattccaac aacttggttg acagaatgtt     1080
acgtaggccg gccaatgtgg ctgtggtttc agggtccata aagcttttca attcatcttt     1140
tttttttttg ttcttttttt tgattccggt ttctttgaaa ttttttttgat tcggtaatct    1200 ccgagcagaa ggaagaacga aggaaggagc acagacttag attggtatat atacgcatat     1260
gtggtgttga agaaacatga aattgcccag tattcttaac ccaactgcac agaacaaaaa     1320
cctgcaggaa acgaagataa atcatgtcga aagctacata taaggaacgt gctgctactc     1380
atcctagtcc tgttgctgcc aagctattta atatcatgca cgaaaagcaa acaaacttgt     1440
gtgcttcatt ggatgttcgt accaccaagg aattactgga gttagttgaa gcattaggtc     1500
ccaaaatttg tttactaaaa acacatgtgg atatcttgac tgattttttcc atggagggca    1560 cagttaagcc gctaaaggca ttatccgcca agtacaattt tttactcttc gaagacagaa     1620
aatttgctga cattggtaat acagtcaaat gcagtactc tgcgggtgta tacagaatag      1680
cagaatgggc agacattacg aatgcacacg tgtggtggg cccaggtatt gttagcggtt      1740
tgaagcaggc ggcggaagaa gtaacaaagg aacctagagg cctttttgatg ttagcagaat    1800 tgtcatgcaa gggctcccta gctactggag aatatactaa gggtactgtt gacattgcga     1860
agagcgacaa agattttgtt atcggcttta ttgctcaaag agacatgggt ggaagagatg     1920
aaggttacga ttggttgatt atgacacccg gtgtgggttt agatgacaag ggagacgcat     1980
tgggtcaaca gtatagaacc gtggatgatg tggtctctac aggatctgac attattattg     2040
ttggaagagg actatttgca aagggaaggg atgctaaggt agagggtgaa cgttacagaa     2100
aagcaggctg ggaagcatat ttgagaagat gcggccagca aaactaaaaa actgtattat     2160
aagtaaatgc atgtatacta aactcacaaa ttagagcttc aatttaatta tatcagttat     2220
tacccgggaa tctcggtcgt aatgattttct ataatgacga aaaaaaaaa attggaaaga    2280 aaaagcttca tggccttgcg gccgcttcat atatgacgta ataaatgaa atgtagattc      2340 attttgtaga ttcctatatc ctcagagaga attttttggta tatcctatat gcataatatt    2400
atagtctttg ccaacaatcg aaaccaaaca tatatcttaa aatacaccac tttctcaaat     2460
aaattcgtta aataacggtg tgttgaaatg tttaccgtaa cttgtaacag ctctaacaac    2520
tcatacctgc tatgtactga ttccaagaaa aaaattaat taatctagag tcgacctgca    2580
ggcatgcaag cttggcgtaa tcatggtcat agctgtttcc tgtgtgaaat tgttatccgc     2640
tcacaattcc acacaacata cgagccggaa gcataaagtg taaagcctgg ggtgcctaat     2700
gagtgagcta actcacatta attgcgttgc gctcactgcc cgctttccag tcgggaaacc     2760
tgtcgtgcca gctgcattaa tgaatcggcc aacgcgcggg gagaggcggt ttgcgtattg     2820
ggcgctcttc cgcttcctcg ctcactgact cgctgcgctc ggtcgttcgg ctgcggcgag     2880
cggtatcagc tcactcaaag gcggtaatac ggttatccac agaatcaggg gataacgcag     2940
gaaagaacat gtgagcaaaa ggccagcaaa aggccaggaa ccgtaaaaag gccgcgttgc     3000
tggcgttttt ccataggctc cgcccccctg acgagcatca caaaaatcga cgctcaagtc     3060
```

```
agaggtggcg aaacccgaca ggactataaa gataccaggc gtttccccct ggaagctccc    3120
tcgtgcgctc tcctgttccg accctgccgc ttaccggata cctgtccgcc tttctccctt    3180
cgggaagcgt ggcgctttct catagctcac gctgtaggta tctcagttcg gtgtaggtcg    3240
ttcgctccaa gctgggctgt gtgcacgaac cccccgttca gcccgaccgc tgcgccttat    3300
ccggtaacta tcgtcttgag tccaacccgg taagacacga cttatcgcca ctggcagcag    3360
ccactggtaa caggattagc agagcgaggt atgtaggcgg tgctacagag ttcttgaagt    3420
ggtggcctaa ctacggctac actagaagga cagtatttgg tatctgcgct ctgctgaagc    3480
cagttacctt cggaaaaaga gttggtagct cttgatccgg caaacaaacc accgctggta    3540
gcggtggttt ttttgtttgc aagcagcaga ttacgcgcag aaaaaaagga tctcaagaag    3600
atcctttgat cttttctacg gggtctgacg ctcagtggaa cgaaaactca cgttaaggga    3660
ttttggtcat gagattatca aaaggatct tcacctagat ccttttaaat taaaaatgaa    3720
gttttaaatc aatctaaagt atatatgagt aaacttggtc tgacagttac caatgcttaa    3780
tcagtgaggc acctatctca gcgatctgtc tatttcgttc atccatagtt gcctgactcc    3840
ccgtcgtgta gataactacg atacgggagg gcttaccatc tggccccagt gctgcaatga    3900
taccgcgaga cccacgctca ccggctccag atttatcagc aataaaccag ccagccggaa    3960
gggccgagcg cagaagtggt cctgcaactt tatccgcctc catccagtct attaattgtt    4020
gccgggaagc tagagtaagt agttcgccag ttaatagttt gcgcaacgtt gttgccattg    4080
ctacaggcat cgtggtgtca cgctcgtcgt ttggtatggc ttcattcagc tccggttccc    4140
aacgatcaag gcgagttaca tgatccccca tgttgtgcaa aaaagcggtt agctccttcg    4200
gtcctccgat cgttgtcaga agtaagttgg ccgcagtgtt atcactcatg gttatggcag    4260
cactgcataa ttctcttact gtcatgccat ccgtaagatg cttttctgtg actggtgagt    4320
actcaaccaa gtcattctga gaatagtgta tgcggcgacc gagttgctct tgcccggcgt    4380
caatacggga taataccgcg ccacatagca gaactttaaa agtgctcatc attggaaaac    4440
gttcttcggg gcgaaaactc tcaaggatct taccgctgtt gagatccagt tcgatgtaac    4500
ccactcgtgc acccaactga tcttcagcat cttttacttt caccagcgtt tctgggtgag    4560
caaaaacagg aaggcaaaat gccgcaaaaa agggaataag ggcgacacgg aaatgttgaa    4620
tactcatact cttcctttt caatattatt gaagcattta tcagggttat tgtctcatga    4680
gcggatacat atttgaatgt atttagaaaa ataaacaaat aggggttccg cgcacatttc    4740
cccgaaaagt gccacctgac gtctaagaaa ccattattat catgacatta acctataaaa    4800
ataggcgtat cacgaggccc tttcgtc                                        4827
```

<210> SEQ ID NO 11
<211> LENGTH: 20
<212> TYPE: DNA
<213> ORGANISM: artificial sequence
<220> FEATURE:
<223> OTHER INFORMATION: BK1042 primer

<400> SEQUENCE: 11

```
tcttaaaatg ctcttcttat                                                  20
```

<210> SEQ ID NO 12
<211> LENGTH: 20
<212> TYPE: DNA
<213> ORGANISM: artificial sequence
<220> FEATURE:
<223> OTHER INFORMATION: H95 primer

<400> SEQUENCE: 12
cgaaactaat ggaggggagc                                                    20

<210> SEQ ID NO 13
<211> LENGTH: 20
<212> TYPE: DNA
<213> ORGANISM: artificial sequence
<220> FEATURE:
<223> OTHER INFORMATION: BK1043 primer

<400> SEQUENCE: 13
acaatggaat ttcgacaatt                                                    20

<210> SEQ ID NO 14
<211> LENGTH: 22
<212> TYPE: DNA
<213> ORGANISM: artificial sequence
<220> FEATURE:
<223> OTHER INFORMATION: 92 primer

<400> SEQUENCE: 14
gagaagatgc ggccagcaaa ac                                                 22

<210> SEQ ID NO 15
<211> LENGTH: 20
<212> TYPE: DNA
<213> ORGANISM: artificial sequence
<220> FEATURE:
<223> OTHER INFORMATION: H96 primer

<400> SEQUENCE: 15
taacgcctgt ctgtagcgct                                                    20

<210> SEQ ID NO 16
<211> LENGTH: 3078
<212> TYPE: DNA
<213> ORGANISM: Kluyveromyces lactis

<400> SEQUENCE: 16
atgtcttgtt tgatcccaga aaacctaaga aatccaaaga aagttcacga aaacagattg        60
ccaaccaggg cttactacta cgaccaagat atcttcgaat ccttaaacgg tccttgggct       120
tttgccttat tcgacgctcc cttggatgct ccagacgcca agaacttgga ttgggaaact       180
gccaagaaat ggtctactat ttccgttcca tctcactggg aactacaaga ggactggaaa       240
tacggcaagc caatctacac caacgtccaa tacccaatac ctatcgacat tccaaaccct       300
ccgaccgtca atccaactgg tgtttacgct cgtactttcg aattggactc caagtctatc       360
gaaagtttcg agcacagatt gcgtttcgaa ggtgtcgata actgttacga attgtacgtc       420
aacggtcaat acgttggctt caacaagggt tccagaaatg agccgaattc gatatacaa        480 aagtacgttt ccgagggcga aaacttggtt gttgtcaaag tgttcaagtg gtccgactct       540
acttacatcg aagaccaaga tcaatggtgg ttatctggta tctacagaga cgtctctttg       600
ttaaagctac caaagaaagc tcacatcgaa gacgtcagag ttacaaccac tttcgtcgat       660
tctcaatacc aagcgccga attgtctgtt aaggtggatg tccaaggcag ttcttacgat       720
cacatcaact tcaccttgta cgagccagaa gacggttcca agtttacga cgcttcttcc       780 ttgctaaacg aagagaatgg caacaccact ttttctacaa aggaattcat ttccttttct       840
accaagaaaa acgaagagac tgctttcaag atcaacgtca aagctccaga acactggact       900

-continued

```
gccgagaacc caaccttgta caagtaccaa ctggatttga ttggctccga cggttcagtt      960
attcaatcta tcaagcacca tgtcggtttc agacaagtgg aattgaagga tggcaatatc     1020
accgtcaacg gcaaggacat cttgttccgt ggtgtcaaca gacacgacca ccatccacgt     1080
ttcggcagag ctgtcccatt ggatttcgtt gtcagagact taatcttgat gaagaaattc     1140
aacatcaatg ctgtcagaaa ctctcattac ccaaatcacc ccaaggttta cgatttgttc     1200
gacaagctgg ttttgggt tatcgacgaa gccgatttgg agaccacgg tgttcaagaa        1260
ccattcaaca gacacaccaa tttggaagcc gagtacccag acaccaagaa caaattgtac     1320
gacgtcaacg ctcactactt gtccgacaac ccagaatacg aggttgctta cttggacaga     1380
gcctctcaat tggttttacg tgacgtcaac cacccatcca tcatcatttg gtctttgggc     1440
aacgaagcct gttacggcag aaaccacaag gctatgtaca aactaatcaa gcaactggac     1500
ccaaccagat tggttcacta cgaaggcgac ttaaacgctt tgtctgccga catcttctcc     1560
tttatgtacc caaccttcga aatcatggag cgttggagaa agaatcacac cgacgaaaac     1620
ggcaagttcg agaaaccatt gattctatgc gaatacggtc acgctatggg caacggacca     1680
ggttctttga agagtacca agaattgttt tacaaagaga agttctacca aggtggcttt      1740
atctgggaat gggccaacca cggtatcgaa ttcgaggacg tttctactgc cgatggcaag     1800
ttgcacaaag cctacgctta cggtggcgat ttcaaggaag aggtccacga cggtgttttc     1860
attatgacg tttgtgcaa cagcgaacac aatccaactc ctggtttggt cgaatacaag      1920
aaagttatcg aaccagtcca catcaagatt gctcatggtt ctgttactat caccaacaag    1980
cacgatttca ttactacaga ccacttgtta ttcatcgaca agatactgg caagaccatc      2040
gacgttccgt ctttgaagcc agaagagtct gttaccattc catccgatac tacatacgtt    2100
gtcgctgtgt tgaaggacga tgccggtgtt ttgaaggctg ccacgaaat tgcttggggt      2160
caagccgaac tacctttgaa ggtcccagac ttcgttaccg aaactgccga gaaagccgct    2220
aagatcaacat gtggaaaaag atacgtttcc gtcgaatctt caggttaca cttcatcctg    2280
gacaagttat tgggcaaaat cgaatctttg aaggtcaagg gaaagaaat ctcttccaag      2340
ttcgaaggtt cttcaattac tttctggaga ccacctacca caacgacga accaagagat    2400
ttcaagaact ggaagaaata caatatcgac ttgatgaagc aaaacattca cggagtttct    2460
gtcgaaaagg gttccaacgg ctcttttggct gtggttactg tcaacagcag aatttctcca   2520
gttgtctttt actacggttt cgaaactgtc caaaagtaca ccattttcgc caacaagatc    2580
aatttgaaca cctctatgaa gttaactggc gaataccaac ctcccgactt cccaagagtt    2640
ggttacgaat tctggttggg cgactcttac gaatccttcg agtggttggg cagaggtcct    2700
ggagaatctt acccagacaa aaaggaatct caaagattcg gtttgtacga ttccaaggac    2760
gtcgaggaat tcgtttacga ttacccacaa gaaaacggaa atcacaccga tactcatttc    2820
ttgaacatca agtttgaagg tgctggcaag ttatctatct tccaaaagga aaaaccattc    2880
aacttcaaga tttccgacga gtacggtgtc gatgaagccg ctcacgcttg cgacgtcaag    2940
agatacggtc gtcactacct aagattggac catgctattc acggtgttgg ctccgaagcc    3000
tgtggtccag ctgttttgga ccaatacaga ctaaaggctc aagacttcaa cttcgaattt    3060
gacttggctt tcgaatag                                                   3078
```

<210> SEQ ID NO 17
<211> LENGTH: 1700
<212> TYPE: DNA
<213> ORGANISM: artificial sequence
<220> FEATURE:
<223> OTHER INFORMATION: 5' end of beta-galactosidase coding region from Kluyveromyces lactis

<400> SEQUENCE: 17

```
atgtcttgtt tgatcccaga aaacctaaga aatccaaaga aagttcacga aaacagattg      60
ccaaccaggg cttactacta cgaccaagat atcttcgaat ccttaaacgg tccttgggct     120
tttgccttat tcgacgctcc cttggatgct ccagacgcca agaacttgga ttgggaaact     180
gccaagaaat ggtctactat ttccgttcca tctcactggg aactacaaga ggactggaaa     240
tacggcaagc aatctacac caacgtccaa tacccaatac ctatcgacat ccaaacccct     300
ccgaccgtca atccaactgg tgtttacgct cgtactttcg aattggactc caagtctatc     360
gaaagtttcg agcacagatt gcgtttcgaa ggtgtcgata actgttacga attgtacgtc     420
aacggtcaat acgttggctt caacaagggt tccagaaatg gagccgaatt cgatatacaa     480
aagtacgttt ccgagggcga aaacttggtt gttgtcaaag tgttcaagtg gtccgactct     540
acttacatcg aagaccaaga tcaatggtgg ttatctggta tctacagaga cgtctctttg     600
ttaaagctac caaagaaagc tcacatcgaa gacgtcagag ttacaaccac tttcgtcgat     660
tctcaatacc aagacgccga attgtctgtt aaggtggatg tccaaggcag ttcttacgat     720
cacatcaact tcaccttgta cgagccagaa gacggttcca agtttacga cgcttcttcc     780
ttgctaaacg aagagaatgg caacaccact ttttctacaa aggaattcat ttcctttttct     840
accaagaaaa acgaagagac tgctttcaag atcaacgtca aagctccaga acactggact     900
gccgagaacc caaccttgta caagtaccaa ctggatttga ttggctccga cggttcagtt     960
attcaatcta tcaagcacca tgtcggttttc agacaagtgg aattgaagga tggcaatatc    1020
accgtcaacg gcaaggacat cttgttccgt ggtgtcaaca gacacgacca ccatccacgt    1080
ttcggcagag ctgtcccatt ggatttcgtt gtcagagact taatcttgat gaagaaattc    1140
aacatcaatg ctgtcagaaa ctctcattac ccaaatcacc ccaaggttta cgatttgttc    1200
gacaagctgg gttttgggt tatcgacgaa gccgatttgg agacccacgg tgttcaagaa    1260
ccattcaaca gacacaccaa tttggaagcc gagtacccag acaccaagaa caaattgtac    1320
gacgtcaacg ctcactactt gtccgacaac ccagaatacg aggttgctta cttggacaga    1380
gcctctcaat ggttttacg tgacgtcaac cacccatcca tcatcatttg gtctttgggc    1440
aacgaagcct gttacggcag aaaccacaag gctatgtaca aactaatcaa gcaactggac    1500
ccaaccgat tggttcacta cgaaggcgac ttaaacgctt tgtctgccga catcttctcc     1560
tttatgtacc caaccttcga aatcatggag cgttggagaa agaatcacac cgacgaaaac    1620
ggcaagttcg agaaaccatt gattctatgc gaatacggtc acgctatggg caacggacca    1680
ggttctttga aagagtacca                                                  1700
```

<210> SEQ ID NO 18
<211> LENGTH: 1438
<212> TYPE: DNA
<213> ORGANISM: artificial sequence
<220> FEATURE:
<223> OTHER INFORMATION: 3' end of beta-galactosidase coding region from Kluyveromyces lactis

<400> SEQUENCE: 18

```
gattctatgc gaatacggtc acgctatggg caacggacca ggttctttga aagagtacca      60
agaattgttt tacaaagaga agttctacca aggtggcttt atctgggaat gggccaacca     120
```

| | |
|---|---|
| cggtatcgaa ttcgaggacg tttctactgc cgatggcaag ttgcacaaag cctacgctta | 180 |
| cggtggcgat ttcaaggaag aggtccacga cggtgttttc attatggacg gtttgtgcaa | 240 |
| cagcgaacac aatccaactc ctggtttggt cgaatacaag aaagttatcg aaccagtcca | 300 |
| catcaagatt gctcatggtt ctgttactat caccaacaag cacgatttca ttactacaga | 360 |
| ccacttgtta ttcatcgaca agatactgg caagaccatc gacgttccgt ctttgaagcc | 420 |
| agaagagtct gttaccattc catccgatac tacatacgtt gtcgctgtgt tgaaggacga | 480 |
| tgccggtgtt ttgaaggctg ccacgaaat tgcttggggt caagccgaac tacctttgaa | 540 |
| ggtcccagac ttcgttaccg aaactgccga gaaagccgct aagatcaacg atggaaaaag | 600 |
| atacgtttcc gtcgaatctt caggtttaca cttcatcctg dacaagttat tgggcaaaat | 660 |
| cgaatctttg aaggtcaagg gaaaagaaat ctcttccaag ttcgaaggtt cttcaattac | 720 |
| tttctggaga ccacctacca acaacgacga accaagagat ttcaagaact ggaagaaata | 780 |
| caatatcgac ttgatgaagc aaaacattca cggagtttct gtcgaaaagg gttccaacgg | 840 |
| ctctttggct gtggttactg tcaacagcag aatttctcca gttgtctttt actacggttt | 900 |
| cgaaactgtc caaaagtaca ccattttcgc caacaagatc aatttgaaca cctctatgaa | 960 |
| gttaactggc gaataccaac ctcccgactt cccaagagtg ggttacgaat ctgttgggg | 1020 |
| cgactcttac gaatccttcg agtggttggg cagaggtcct ggagaatctt acccagacaa | 1080 |
| aaaggaatct caaagattcg gtttgtacga ttccaaggac gtcgaggaat cgtttacga | 1140 |
| ttacccacaa gaaaacggaa atcacaccga tactcatttc ttgaacatca agtttgaagg | 1200 |
| tgctggcaag ttatctatct tccaaaagga aaaaccattc aacttcaaga tttccgacga | 1260 |
| gtacggtgtc gatgaagccg ctcacgcttg cgacgtcaag agatacggtc gtcactacct | 1320 |
| aagattggac catgctattc acggtgttgg ctccgaagcc tgtggtccag ctgttttgga | 1380 |
| ccaatacaga ctaaaggctc aagacttcaa cttcgaattt gacttggctt tcgaatag | 1438 |

<210> SEQ ID NO 19
<211> LENGTH: 60
<212> TYPE: DNA
<213> ORGANISM: artificial sequence
<220> FEATURE:
<223> OTHER INFORMATION: H98 primer

<400> SEQUENCE: 19

| | |
|---|---|
| ttaccctacc agcaatataa gtaaaaaact atgtcttgtt tgatcccaga aaacctaaga | 60 |

<210> SEQ ID NO 20
<211> LENGTH: 17
<212> TYPE: DNA
<213> ORGANISM: artificial sequence
<220> FEATURE:
<223> OTHER INFORMATION: M13ForTOPO primer

<400> SEQUENCE: 20

| | |
|---|---|
| gtaaaacgac ggccagt | 17 |

<210> SEQ ID NO 21
<211> LENGTH: 22
<212> TYPE: DNA
<213> ORGANISM: artificial sequence
<220> FEATURE:
<223> OTHER INFORMATION: M13RevTOPO primer

<400> SEQUENCE: 21

| | |
|---|---|
| cacacaggaa acagctatga cc | 22 |

<210> SEQ ID NO 22
<211> LENGTH: 60
<212> TYPE: DNA
<213> ORGANISM: artificial sequence
<220> FEATURE:
<223> OTHER INFORMATION: H99 primer

<400> SEQUENCE: 22

```
agtttccagc acttgatatt attttcctct ctattcgaaa gccaagtcaa attcgaagtt    60
```

<210> SEQ ID NO 23
<211> LENGTH: 9585
<212> TYPE: DNA
<213> ORGANISM: artificial sequence
<220> FEATURE:
<223> OTHER INFORMATION: PmeI digested pHR81-ILV5p-R8B2y2 plasmid

<400> SEQUENCE: 23

```
ggccgcacct ggtaaaacct ctagtggagt agtagatgta atcaatgaag cggaagccaa      60
aagaccagag tagaggccta tagaagaaac tgcgatacct tttgtgatgg ctaaacaaac     120
agacatcttt ttatatgttt ttacttctgt atatcgtgaa gtagtaagtg ataagcgaat     180
ttggctaaga acgttgtaag tgaacaaggg acctcttttg cctttcaaaa aaggattaaa     240
tggagttaat cattgagatt tagttttcgt tagattctgt atccctaaat aactccctta     300
cccgacggga aggcacaaaa gacttgaata atagcaaacg gccagtagcc aagaccaaat     360
aatactagag ttaactgatg gtcttaaaca ggcattacgt ggtgaactcc aagaccaata     420
tacaaaatat cgataagtta tccttgccca ccaatttaag gagcctacat caggacagta     480
gtaccattcc tcagagaaga ggtatacata acaagaaaat cgcgtgaaca ccttatataa     540
cttagcccgt tattgagcta aaaaaccttg caaaatttcc tatgaataag aatacttcag     600
acgtgataaa aatttacttt ctaactcttc tcacgctgcc cctatctgtt cttccgctct     660
accgtgagaa ataaagcatc gagtacggca gttcgctgtc actgaactaa acaataagg     720
ctagttcgaa tgatgaactt gcttgctgtc aaacttctga gttgccgctg atgtgacact     780
gtgacaataa attcaaaccg gttatagcgg tctcctccgg taccggttct gccacctcca     840
atagagctca gtaggagtca gaacctctgc ggtggctgtc agtgactcat ccgcgtttcg     900
taagttgtgc gcgtgcacat ttcgcccgtt cccgctcatc ttgcagcagg cgaaattttc     960
atcacgctgt aggacgcaaa aaaaaataa ttaatcgtac aagaatcttg gaaaaaaaat    1020
tgaaaaattt tgtataaaag ggatgaccta acttgactca atggctttta cacccagtat    1080
tttcccttc cttgtttgtt acaattatag aagcaagaca aaaacatata gacaacctat    1140
tcctaggagt tatatttttt taccctacca gcaataatag taaaaaactg tttaaacagt    1200
atgaaggttt tctacgacaa ggattgtgac ttgtctatca ttcaaggtaa aaaggtcgcc    1260
atcatcggtt ttggttccca aggtcacgct caagccttga acttaaagga ctctggtgtc    1320
gatgttaccg tcggtctacc aaagggtttc gctgacgttg ccaaggccga agctcacggt    1380
ttcaaggtta ctgacgtcgc cgctgccgtt gctggtgctg atttggtcat gatcctaatt    1440
ccagacgaat ccaatcccca attgtacaaa acgaaatcg aaccaaacat caaaagggt    1500
gccactttgg ctttctccca cggtttcgct atccactaca accaagttgt tccaagagct    1560
gacttggacg ttatcatgat tgctcctaag gctccaggtc ataccgttag atctgaattc    1620
gtcaagggtg gtgtatccc agacttgatt gctgtttacc aagacgtttc tggtaatgcc    1680
```

```
aaaaacgtcg ctttgtccta cgctgccggt gttggtggtg gtcgtactgg tatcatcgaa    1740
actaccttca aggacgaaac cgaaaccgac ttattcggtg aacaagctgt tttgtgtggt    1800
ggtaccgtcg aattggtcaa ggctggtttt gaaactttgg tcgaagctgg ttacgctcca    1860
gaaatggctt acttcgaatg tttacacgaa ttgaagttga ttgttgattt gatgtacgaa    1920
ggtggtattg ctaacatgaa ctactctatc tctaacaacg ctgaatacgg tgaatacgtt    1980
actggtccag aagtcattaa cgccgaatct agacaagcta tgagaaatgc tttgaagaga    2040
attcaagatg gtgaattcgc taagatgttc atctctgaag gtgctaccgg ttacccttct    2100
atgactgcta agcgtagaaa caacgctgct cacggtatcg aaatcatcgg tgaacaacta    2160
agagctatga tgccatggat tggtgctaac aagatcgtcg ataagagaaa aaactgaagg    2220
ccctgcaggc cagaggaaaa taatatcaag tgctggaaac ttttctctt ggaattttg    2280 caacatcaag tcatagtcaa ttgaattgac ccaatttcac atttaagatt tttttttttt    2340
catccgacat acatctgtac actaggaagc cctgttttc tgaagcagct tcaaatatat    2400
atatttttta catatttatt atgattcaat gaacaatcta attaaatcga aaacaagaac    2460
cgaaacgcga ataaataatt tatttagatg gtgacaagtg tataagtcct catcgggaca    2520
gctacgattt ctctttcggt tttggctgag ctactggttg ctgtgacgca gcggcattag    2580
cgcggcgtta tgagctaccc tcgtggcctg aaagatggcg gaataaagc ggaactaaaa    2640 attactgact gagccatatt gaggtcaatt tgtcaactcg tcaagtcacg tttggtggac    2700
ggcccctttc caacgaatcg tatatactaa catgcgcgcg cttcctatat acacatatac    2760 atatatat atatatatgt gtgcgtgtat gtgtacacct gtatttaatt tccttactcg    2820 cgggttttc ttttttctca attcttggct tcctcttct cgagcggacc ggatcctccg    2880
cggtgccggc agatctattt aaatggcgcg ccgacgtcag gtggcacttt tcggggaaat    2940
gtgcgcggaa cccctatttg tttattttc taaatacatt caaatatgta tccgctcatg    3000
agacaataac cctgataaat gcttcaataa tattgaaaaa ggaagagtat gagtattcaa    3060
catttccgtg tcgcccttat tcccttttt gcggcatttt gccttcctgt ttttgctcac    3120
ccagaaacgc tggtgaaagt aaaagatgct gaagatcagt tgggtgcacg agtgggttac    3180
atcgaactgg atctcaacag cggtaagatc cttgagagtt ttcgccccga agaacgtttt    3240
ccaatgatga gcacttttaa agttctgcta tgtggcgcgg tattatcccg tattgacgcc    3300
gggcaagagc aactcggtcg ccgcatacac tattctcaga atgacttggt tgagtactca    3360
ccagtcacag aaaagcatct tacggatggc atgacagtaa gagaattatg cagtgctgcc    3420
ataaccatga gtgataacac tgcggccaac ttacttctga caacgatcgg aggaccgaag    3480
gagctaaccg cttttttgca acatgggg gatcatgtaa ctcgccttga tcgttgggaa    3540
ccggagctga atgaagccat accaaacgac gagcgtgaca ccacgatgcc tgtagcaatg    3600
gcaacaacgt tgcgcaaact attaactggc gaactactta ctctagcttc ccggcaacaa    3660
ttaatagact ggatggaggc ggataaagtt gcaggaccac ttctgcgctc ggcccttccg    3720
gctggctggt ttattgctga taaatctgga gccggtgagc gtggttctcg cggtatcatt    3780
gcagcactgg ggccagatgg taagccctcc cgtatcgtag ttatctacac gacggggagt    3840
caggcaacta tggatgaacg aaatagacag atcgctgaga taggtgcctc actgattaag    3900
cattggtaac tgtcagacca agtttactca tatatacttt agattgattt aaaacttcat    3960
ttttaattta aaaggatcta ggtgaagatc ctttttgata atctcatgac caaaatccct    4020
taacgtgagt tttcgttcca ctgagcgtca gaccccgtag aaaagatcaa aggatcttct    4080
```

```
tgagatcctt tttttctgcg cgtaatctgc tgcttgcaaa caaaaaaacc accgctacca    4140
gcggtggttt gtttgccgga tcaagagcta ccaactcttt ttccgaaggt aactggcttc    4200
agcagagcgc agataccaaa tactgttctt ctagtgtagc cgtagttagg ccaccacttc    4260
aagaactctg tagcaccgcc tacatacctc gctctgctaa tcctgttacc agtggctgct    4320
gccagtggcg ataagtcgtg tcttaccggg ttggactcaa gacgatagtt accggataag    4380
gcgcagcggt cgggctgaac ggggggttcg tgcacacagc ccagcttgga gcgaacgacc    4440
tacaccgaac tgagatacct acagcgtgag ctatgagaaa gcgccacgct cccgaaggg    4500 agaaggcgca caggtatcc ggtaagcggc agggtcggaa caggagagcg cacgagggag    4560
cttccagggg gaaacgcctg gtatctttat agtcctgtcg ggtttcgcca cctctgactt    4620
gagcgtcgat ttttgtgatg ctcgtcaggg gggcggagcc tatggaaaaa cgccagcaac    4680
gcggcctttt tacggttcct ggccttttgc tggccttttg ctcacatgtt ctttcctgcg    4740 ttatccctg attctgtgga taaccgtatt accgcctttg agtgagctga taccgctcgc    4800
cgcagccgaa cgaccgagcg cagcgagtca gtgagcgagg aagcggaaga gcgcccaata    4860
cgcaaaccgc ctctccccgc gcgttggccg attcattaat gcagctggca cgacaggttt    4920
cccgactgga aagcgggcag tgagcgcaac gcaattaatg tgagttagct cactcattag    4980 gcacccagg cttacactt tatgcttccg gctcgtatgt tgtgtggaat tgtgagcgga    5040
taacaatttc acacaggaaa cagctatgac catgattacg ccaagctttt ctttccaat    5100 tttttttttt tcgtcattat aaaaatcatt acgaccgaga ttcccgggta ataactgata    5160
taattaaatt gaagctctaa tttgtgagtt tagtatacat gcatttactt ataatacagt    5220
tttttagttt tgctggccgc atcttctcaa atatgcttcc cagcctgctt ttctgtaacg    5280
ttcaccctct accttagcat cccttccctt tgcaaatagt cctcttccaa caataataat    5340
gtcagatcct gtagagacaa catcatccac ggttctatac tgttgaccca atgcatctcc    5400
cttgtcatct aaacccacac cgggtgtcat aatcaaccaa tcgtaacctt catctcttcc    5460
acccatgtct ctttgagcaa taaagccgat aacaaaatct ttgtcgctct tcgcaatgtc    5520
aacagtaccc ttagtatatt ctccagtaga tagggagccc ttgcatgaca attctgctaa    5580
catcaaaagg cctctaggtt cctttgttac ttcttctgcc gcctgcttca aaccgctaac    5640
aatacctggg cccaccacac cgtgtgcatt cgtaatgtct gcccattctg ctattctgta    5700
tacacccgca gagtactgca atttgactgt attaccaatg tcagcaaatt ttctgtcttc    5760
gaagagtaaa aaattgtact tggcggataa tgcctttagc ggcttaactg tgccctccat    5820
ggaaaaatca gtcaagatat ccacatgtgt tttagtaaa caatttttgg gacctaatgc    5880
ttcaactaac tccagtaatt ccttggtggt acgaacatcc aatgaagcac acaagtttgt    5940
ttgcttttcg tgcatgatat taaatagctt ggcagcaaca ggactaggat gagtagcagc    6000
acgttcctta tatgtagctt tcgacatgat ttatcttcgt ttcctgcagg ttttttgttct    6060 gtgcagttgg gttaagaata ctgggcaatt tcatgtttct tcaacactac atatgcgtat    6120
atataccaat ctaagtctgt gctccttcct tcgttcttcc ttctgttcgg agattaccga    6180
atcaaaaaaa tttcaaggaa accgaaatca aaaaaagaa taaaaaaaaa atgatgaatt    6240
gaaaagcttg catgcctgca ggtcgactct agtatactcc gtctactgta cgatacactt    6300
ccgctcaggt ccttgtcctt taacgaggcc ttaccactct tttgttactc tattgatcca    6360
gctcagcaaa ggcagtgtga tctaagattc tatcttcgcg atgtagtaaa actagctaga    6420
```

```
ccgagaaaga gactagaaat gcaaaaggca cttctacaat ggctgccatc attattatcc   6480
gatgtgacgc tgcatttttt tttttttttt tttttttttt tttttttttt tttttttttt   6540
tttttgtac aaatatcata aaaaagaga atcttttaa gcaaggattt tcttaacttc   6600
ttcggcgaca gcatcaccga cttcggtggt actgttggaa ccacctaaat caccagttct   6660
gatacctgca tccaaaacct ttttaactgc atcttcaatg gctttaccct cttcaggcaa   6720
gttcaatgac aatttcaaca tcattgcagc agacaagata gtggcgatag ggttgacctt   6780
attctttggc aaatctggag cggaaccatg gcatggttcg tacaaaccaa atgcggtgtt   6840
cttgtctggc aaagaggcca aggacgcaga tggcaacaaa cccaaggagc tgggataac   6900
ggaggcttca tcggagatga tatcaccaaa catgttgctg gtgattataa taccatttag   6960
gtgggttggg ttcttaacta ggatcatggc ggcagaatca atcaattgat gttgaacttt   7020
caatgtaggg aattcgttct tgatggtttc ctccacagtt tttctccata atcttgaaga   7080
ggccaaaaca ttagctttat ccaaggacca aataggcaat ggtggctcat gttgtagggc   7140
catgaaagcg gccattcttg tgattctttg cacttctgga acggtgtatt gttcactatc   7200
ccaagcgaca ccatcaccat cgtcttcctt tctcttacca agtaaatac ctcccactaa   7260
ttctctaaca acaacgaagt cagtaccttt agcaaattgt ggcttgattg gagataagtc   7320
taaaagagag tcggatgcaa agttacatgg tcttaagttg gcgtacaatt gaagttcttt   7380
acggattttt agtaaacctt gttcaggtct aacactaccg gtaccccatt taggaccacc   7440
cacagcacct aacaaaacgg catcagcctt cttggaggct tccagcgcct catctggaag   7500
tggaacacct gtagcatcga tagcagcacc accaattaaa tgattttcga aatcgaactt   7560
gacattggaa cgaacatcag aaatagcttt aagaacctta atggcttcgg ctgtgatttc   7620
ttgaccaacg tggtcacctg gcaaaacgac gatcttctta ggggcagaca ttacaatggt   7680
atatccttga aatatatata aaaaaaaaa aaaaaaaaa aaaaaaaat gcagcttctc   7740
aatgatattc gaatacgctt tgaggagata cagcctaata tccgacaaac tgttttacag   7800
atttacgatc gtacttgtta cccatcattg aattttgaac atccgaacct gggagttttc   7860
cctgaaacag atagtatatt tgaacctgta taataatata tagtctagcg ctttacggaa   7920
gacaatgtat gtatttcggt tcctggagaa actattgcat ctattgcata ggtaatcttg   7980
cacgtcgcat ccccggttca ttttctgcgt ttccatcttg cacttcaata gcatatcttt   8040
gttaacgaag catctgtgct tcattttgta gaacaaaaat gcaacgcgag agcgctaatt   8100
tttcaaacaa agaatctgag ctgcattttt acagaacaga aatgcaacgc gaaagcgcta   8160
ttttaccaac gaagaatctg tgcttcattt ttgtaaaaca aaaatgcaac gcgagagcgc   8220
taattttcca aacaaagaat ctgagctgca ttttacaga acagaaatgc aacgcgagag   8280
cgctatttta ccaacaaaga atctatactt cttttttgtt ctacaaaaat gcatcccgag   8340
agcgctattt ttctaacaaa gcatcttaga ttactttttt tctcctttgt gcgctctata   8400
atgcagtctc ttgataactt tttgcactgt aggtccgtta aggttagaag aaggctactt   8460
tggtgtctat tttctcttcc ataaaaaag cctgactcca cttcccgcgt ttactgatta   8520
ctagcgaagc tgcgggtgca ttttttcaag ataaaggcat ccccgattat attctatacc   8580
gatgtggatt gcgcatactt tgtgaacaga agtgatagc gttgatgatt cttcattggt   8640
cagaaaatta tgaacggttt cttctatttt gtctctatat actacgtata ggaaatgttt   8700
acattttcgt attgttttcg attcactcta tgaatagttc ttactacaat ttttttgtct   8760
aaagagtaat actagagata aacataaaaa atgtagaggt cgagtttaga tgcaagttca   8820
```

-continued

| | |
|---|---|
| aggagcgaaa ggtggatggg taggttatat agggatatag cacagagata tatagcaaag | 8880 |
| agatacttt gagcaatgtt tgtggaagcg gtattcgcaa tatttagta gctcgttaca | 8940 |
| gtccggtgcg tttttggttt tttgaaagtg cgtcttcaga gcgcttttgg ttttcaaaag | 9000 |
| cgctctgaag ttcctatact ttctagaaa taggaactc ggaataggaa cttcaaagcg | 9060 |
| tttccgaaaa cgagcgcttc cgaaaatgca acgcgagctg cgcacataca gctcactgtt | 9120 |
| cacgtcgcac ctatatctgc gtgttgcctg tatatatata tacatgagaa gaacggcata | 9180 |
| gtgcgtgttt atgcttaaat gcgtacttat atgcgtctat ttatgtagga tgaaaggtag | 9240 |
| tctagtacct cctgtgatat tatcccattc catgcggggt atcgtatgct tccttcagca | 9300 |
| ctacccttta gctgttctat atgctgccac tcctcaattg gattagtctc atccttcaat | 9360 |
| gctatcattt cctttgatat tggatcatat gcatagtacc gagaaactag aggatctccc | 9420 |
| attaccgaca tttgggcgct atacgtgcat atgttcatgt atgtatctgt atttaaaaca | 9480 |
| cttttgtatt attttctc atatatgtgt ataggtttat acggatgatt taattattac | 9540 |
| ttcaccaccc tttatttcag gctgatatct tagccttgtt actag | 9585 |

<210> SEQ ID NO 24
<211> LENGTH: 1089
<212> TYPE: DNA
<213> ORGANISM: Saccharomyces cerevisiae

<400> SEQUENCE: 24

| | |
|---|---|
| tttgtgatgg ctaaacaaac agacatcttt ttatatgttt ttacttctgt atatcgtgaa | 60 |
| gtagtaagtg ataagcgaat ttggctaaga acgttgtaag tgaacaaggg acctcttttg | 120 |
| cctttcaaaa aaggattaaa tggagttaat cattgagatt tagttttcgt tagattctgt | 180 |
| atccctaaat aactccctta cccgacggga aggcacaaaa gacttgaata atagcaaacg | 240 |
| gccagtagcc aagaccaaat aatactgag ttaactgatg gtcttaaaca ggcattacgt | 300 |
| ggtgaactcc aagaccaata tacaaaatat cgataagtta ttcttgccca ccaatttaag | 360 |
| gagcctacat caggacagta gtaccattcc tcagagaaga ggtatacata acaagaaaat | 420 |
| cgcgtgaaca ccttatataa cttagcccgt tattgagcta aaaaaccttg caaaatttcc | 480 |
| tatgaataag aatacttcag acgtgataaa aatttactt ctaactcttc tcacgctgcc | 540 |
| cctatctgtt cttccgctct accgtgagaa ataaagcatc gagtacggca gttcgctgtc | 600 |
| actgaactaa aacaataagg ctagttcgaa tgatgaactt gcttgctgtc aaacttctga | 660 |
| gttgccgctg atgtgacact gtgacaataa attcaaaccg gttatagcgg tctcctccgg | 720 |
| taccggttct gccacctcca atagagctca gtaggagtca gaacctctgc ggtggctgtc | 780 |
| agtgactcat ccgcgtttcg taagttgtgc gcgtgcacat ttcgcccgtt cccgctcatc | 840 |
| ttgcagcagg cgaaattttc atcacgctgt aggacgcaaa aaaaaaataa ttaatcgtac | 900 |
| aagaatcttg gaaaaaaat tgaaaaattt tgtataaaag ggatgaccta acttgactca | 960 |
| atggctttta cacccagtat tttccctttc cttgtttgtt acaattatag aagcaagaca | 1020 |
| aaaacatata gacaacctat tcctaggagt tatatttttt taccctacca gcaatataag | 1080 |
| taaaaaact | 1089 |

<210> SEQ ID NO 25
<211> LENGTH: 627
<212> TYPE: DNA
<213> ORGANISM: Saccharomyces cerevisiae

<400> SEQUENCE: 25

```
agaggaaaat aatatcaagt gctggaaact ttttctcttg gaattttttgc aacatcaagt    60
catagtcaat tgaattgacc caatttcaca tttaagattt ttttttttttc atccgacata   120
catctgtaca ctaggaagcc ctgttttttct gaagcagctt caaatatata tattttttac   180
atatttatta tgattcaatg aacaatctaa ttaaatcgaa aacaagaacc gaaacgcgaa    240
taaataattt atttagatgg tgacaagtgt ataagtcctc atcgggacag ctacgatttc    300
tctttcggtt ttggctgagc tactggttgc tgtgacgcag cggcattagc gcggcgttat    360
gagctaccct cgtggcctga agatggcgg gaataaagcg gaactaaaaa ttactgactg     420
agccatattg aggtcaattt gtcaactcgt caagtcacgt ttggtggacg ccccctttcc    480
aacgaatcgt atatactaac atgcgcgcgc ttcctatata cacatataca tatatatata   540
tatatatgtg tgcgtgtatg tgtacacctg tatttaattt ccttactcgc gggttttttct  600
tttttctcaa ttcttggctt cctcttt                                        627
```

<210> SEQ ID NO 26
<211> LENGTH: 1122
<212> TYPE: DNA
<213> ORGANISM: Escherichia coli

<400> SEQUENCE: 26

```
atgtctaagg ttgctttgat cactggtgtt acaggtcaag acggttctta cttggctgag   60
ttcttgttag aaaagggtta cgaagtacac ggcatcaaga gacgtgcttc tagcttcaac   120
accgaaagag ttgaccatat ctaccaagac ccacacactt gtaacccaaa gttccacttg   180
cattacggtg atttgtccga tacttccaac ttgaccagaa tcttgagaga agtccaacca   240
gatgaagtct acaacttggg tgctatgtct cacgtcgctg tttccttcga atctcctgaa   300
tacaccgctg acgttgacgc tatgggtacc ttaagattgc tagaagctat cagattccta   360
ggcttggaaa agaaaaccag gttttaccaa gcctccacct ctgaattgta cggtttggtg   420
caagaaattc cacaaaagga aaccactcca ttctacccaa gatccccata cgccgtcgct   480
aagttgtacg cctactggat caccgtcaat tacagagaat cttacggtat gtacgcttgt   540
aacggtatct tattcaacca cgaatcccca agacgtggtg aaaccttcgt cactagaaag   600
atcaccagag ccattgctaa cattgctcaa ggtttggaat cctgtttgta cttgggtaac   660
atggactctt tgagagactg gggtcacgcc aaggactacg ttaagatgca atggatgatg   720
ttgcaacaag aacaaccaga agatttcgtt attgctacag gtgttcaata ctctgtcaga   780
caattcgtcg aaatggctgc cgctcaattg ggtatcaagt taagattcga aggtactggt   840
gtcgaagaga agggtattgt tgtctcagtt actggtcacg acgctccagg tgtcaagcct   900
ggtgacgtca tcattgctgt tgatccaaga tacttcagac ccgctgaagt tgaaactttg   960
ctaggtgacc caaccaaggc ccacgaaaag ttgggttgga agccagaaat cactttaaga  1020
gaaatggttt ctgaaatggt cgctaacgat ttggaagctg ccaagaaaca ctctttgcta  1080
aagtctcacg gttacgacgt tgccatcgct ttggaaagtt ag                      1122
```

<210> SEQ ID NO 27
<211> LENGTH: 966
<212> TYPE: DNA
<213> ORGANISM: Escherichia coli

<400> SEQUENCE: 27

```
atgtctaagc aaagagtttt catcgctggt cacagaggta tggtcggtag cgctatcaag    60
agacaattgg aacaaagagg cgacgtcgaa ttggtcttga aaccagaga tgaattgaac    120
ttgttagact caagagctgt tcacgacttc tttgcctctg aatctatcga ccaagtttac    180
ctagctgccg ctaaggtcgg tggcatcgtt gctaacaata cctacccagc tgatttcatt    240
taccaaaaca tgatgatcga atctaacatc attcacgctg cccaccaaaa tgacgtcaac    300
aaattgctat tcttaggtag ttcttgtatc taccctaagt tggccaagca accaatggct    360
gaatccgaat tgctacaagg tactttggaa ccaaccaacg aaccatacgc tattgctaag    420
atcgctggta tcaagttgtg tgaatcctac aacagacaat acggtagaga ctacagatcc    480
gtcatgccaa ccaacttgta cggtccccac gacaacttcc acccatccaa ctctcacgtt    540
atccctgcct tgttaagacg tttccacgaa gctaccgctc aaaacgctcc agacgttgtc    600
gtgtggggtt ctggtacccc aatgagagag ttcttgcacg ttgacgatat ggctgccgct    660
tctattcacg ttatggaatt agctcacgaa gtttggttgg aaaacactca accaatgttg    720
tcccatatca acgttggtac tggtgtcgat tgtactatta gagaattggc tcaaacaatt    780
gccaaggttg tcgattacaa gggtagagtt gtcttcgacg cttctaagcc agacggtact    840
ccaagaaagt tgctagacgt caccagattg caccaattgg ttggtaccat gaaatctcc    900
ttagaagctg gtttggcctc tacttaccaa tggttcttgg aaaaccgtga tcgtttcaga    960
ggttag                                                              966
```

<210> SEQ ID NO 28
<211> LENGTH: 60
<212> TYPE: DNA
<213> ORGANISM: artificial sequence
<220> FEATURE:
<223> OTHER INFORMATION: H17 primer

<400> SEQUENCE: 28

```
acgcaaaata acacagtcaa atcaatcaaa atgtctaagg ttgctttgat cactggtgtt    60
```

<210> SEQ ID NO 29
<211> LENGTH: 60
<212> TYPE: DNA
<213> ORGANISM: artificial sequence
<220> FEATURE:
<223> OTHER INFORMATION: H18 primer

<400> SEQUENCE: 29

```
tcataaatca taagaaattc gcttactcct aactttccaa agcgatggca acgtcgtaac    60
```

<210> SEQ ID NO 30
<211> LENGTH: 60
<212> TYPE: DNA
<213> ORGANISM: artificial sequence
<220> FEATURE:
<223> OTHER INFORMATION: H15 primer

<400> SEQUENCE: 30

```
ataaccataa ccaagtaata catattcaaa tgtctaagca aagagttttc atcgctggtc    60
```

<210> SEQ ID NO 31
<211> LENGTH: 60
<212> TYPE: DNA
<213> ORGANISM: artificial sequence
<220> FEATURE:

<223> OTHER INFORMATION: H16 primer

<400> SEQUENCE: 31
aagatttaaa gtaaattcac ggccctgcag gctaacctct gaaacgatca cggttttcca        60

<210> SEQ ID NO 32
<211> LENGTH: 1713
<212> TYPE: DNA
<213> ORGANISM: Saccharomyces cerevisiae

<400> SEQUENCE: 32
acctggtaaa acctctagtg gagtagtaga tgtaatcaat gaagcggaag ccaaaagacc        60
agagtagagg cctatagaag aaactgcgat acctttgtg atggctaaac aaacagacat       120
ctttttatat gttttactt ctgtatatcg tgaagtagta agtgataagc gaatttggct       180
aagaacgttg taagtgaaca agggacctct tttgcctttc aaaaaggat taaatggagt       240
taatcattga gatttagttt tcgttagatt ctgtatccct aaataactcc cttacccgac       300
gggaaggcac aaaagacttg aataatagca aacggcagt agccaagacc aaataatact       360
agagttaact gatggtctta aacaggcatt acgtggtgaa ctccaagacc aatatacaaa       420
atatcgataa gttattcttg cccaccaatt taaggagcct acatcaggac agtagtacca       480
ttcctcagag aagaggtata cataacaaga aaatcgcgtg aacaccttat ataacttagc       540
ccgttattga gctaaaaaac cttgcaaaat ttcctatgaa taagaatact tcagacgtga       600
taaaaattta ctttctaact cttctcacgc tgccctatc tgttcttccg ctctaccgtg       660
agaaataaag catcgagtac ggcagttcgc tgtcactgaa ctaaacaat aaggctagtt       720
cgaatgatga acttgcttgc tgtcaaactt ctgagttgcc gctgatgtga cactgtgaca       780
ataaattcaa accggttata gcggtctcct ccggtaccgg ttctgccacc tccaatagag       840
ctcccgcacg ccgaaatgca tgcaagtaac ctattcaaag taatatctca tacatgtttc       900
atgagggtaa caacatgcga ctgggtgagc atatgttccg ctgatgtgat gtgcaagata       960
aacaagcaag gcagaaacta acttcttctt catgtaataa acacacccg cgtttattta      1020
cctatctcta aacttcaaca ccttatatca taactaatat ttcttgagat aagcacactg      1080
cacccatacc ttccttaaaa acgtagcttc cagttttgg tggttccggc ttccttcccg      1140
attccgcccg ctaaacgcat atttttgttg cctggtggca tttgcaaaat gcataaccta      1200
tgcatttaaa agattatgta tgctcttctg acttttcgtg tgatgaggct cgtggaaaaa      1260
atgaataatt tatgaatttg agaacaattt tgtgttgtta cggtatttta ctatggaata      1320
atcaatcaat tgaggatttt atgcaaatat cgtttgaata ttttttccgac cctttgagta      1380
cttttcttca taattgcata atattgtccg ctgcccttt ttctgttaga cggtgtcttg      1440
atctacttgc tatcgttcaa caccaccta ttttctaact attttttttt tagctcattt      1500
gaatcagctt atggtgatgg cacatttttg cataaaccta gctgtcctcg ttgaacatag      1560
gaaaaaaaaa tatataaaca aggctctttc actctccttg caatcagatt tgggtttgtt      1620
ccctttattt tcatatttct tgtcatattc ctttctcaat tattatttc tactcataac      1680
ctcacgcaaa ataacacagt caaatcaatc aaa                                   1713

<210> SEQ ID NO 33
<211> LENGTH: 316
<212> TYPE: DNA
<213> ORGANISM: Saccharomyces cerevisiae

<400> SEQUENCE: 33

```
gagtaagcga atttcttatg atttatgatt tttattatta aataagttat aaaaaaaata    60
agtgtataca aattttaaag tgactcttag gttttaaaac gaaaattctt attcttgagt   120
aactcttttcc tgtaggtcag gttgcttttct caggtatagc atgaggtcgc tcttattgac  180
cacacctcta ccggcatgcc gagcaaatgc ctgcaaatcg ctccccattt cacccaattg   240
tagatatgct aactccagca atgagttgat gaatctcggt gtgtattta tgtcctcaga    300
ggacaacacc tgtggt                                                    316
```

<210> SEQ ID NO 34
<211> LENGTH: 725
<212> TYPE: DNA
<213> ORGANISM: artificial sequence
<220> FEATURE:
<223> OTHER INFORMATION: PGK(UAS)-FBA1 hybrid promoter

<400> SEQUENCE: 34

```
aattaccgtc gctcgtgatt tgtttgcaaa agaacaaaa ctgaaaaaac ccagacacgc    60
tcgacttcct gtcttcctat tgattgcagc ttccaatttc gtcacacaac aaggtcctgt   120
cgacgcctac ttggcttcac atacgttgca tacgtcgata tagataataa tgataatgac   180
agcaggatta tcgtaatacg taatagttga aatctcaaa aatgtgtggg tcattacgta    240
ataatgata ggaatgggat tcttctattt ttccttttc cattctagca gccgtcggga    300
aaacgtggca tcctctcttt cgggctcaat tggagtcacg ctgccgtgag catcctctct   360
ttccatatct aacaactgag cacgtaacca atggaaaagc atgagcttag cgttgctcca   420
aaaaagtatt ggatggttaa taccatttgt ctgttctctt ctgactttga ctcctcaaaa   480
aaaaaaaatc tacaatcaac agatcgcttc aattacgccc tcacaaaaac ttttttcctt   540
cttcttcgcc cacgttaaat tttatccctc atgttgtcta acggatttct gcacttgatt   600
tattataaaa agacaaagac ataatacttc tctatcaatt tcagttattg ttcttccttg   660
cgttattctt ctgttcttct ttttcttttg tcatatataa ccataaccaa gtaatacata   720
ttcaa                                                                725
```

<210> SEQ ID NO 35
<211> LENGTH: 580
<212> TYPE: DNA
<213> ORGANISM: Saccharomyces cerevisiae

<400> SEQUENCE: 35

```
gtgaatttac tttaaatctt gcatttaaat aaattttctt tttatagctt tatgacttag    60
tttcaattta tatactattt taatgacatt ttcgattcat tgattgaaag ctttgtgttt   120
tttcttgatg cgctattgca ttgttcttgt ctttttcgcc acatgtaata tctgtagtag   180
atacctgata cattgtggat gctgagtgaa atttagtta ataatggagg cgctcttaat    240
aattttgggg atattggctt tttttttaa agtttacaaa tgaattttt ccgccaggat    300
aacgattctg aagttactct tagcgttcct atcggtacag ccatcaaatc atgcctataa   360
atcatgccta tatttgcgtg cagtcagtat catctacatg aaaaaaactc ccgcaatttc   420
ttatagaata cgttgaaaat taaatgtacg cgccaagata agataacata tatctagatg   480
cagtaatata cacagattcc cgcggacgtg ggaaggaaaa aattagataa caaaatctga   540
gtgatatgga aattccgctg tatagctcat atcttccct                          580
```

<210> SEQ ID NO 36
<211> LENGTH: 1122
<212> TYPE: DNA
<213> ORGANISM: Arabidopsis thaliana

<400> SEQUENCE: 36

| | | |
|---|---|---|
| atggcttctg aaaacaatgg ttctagatcc gactctgaat ctatcaccgc tccaaaggct | 60 |
| gattccaccg ttgtcgaacc aagaaagatc gctttgatca ctggtattac tggtcaagat | 120 |
| ggttcatact tgactgagtt cttgttaggc aagggttacg aagttcacgg tttgatcaga | 180 |
| cgttctagca acttcaacac ccaaagaatc aatcacatct acattgatcc acacaacgtt | 240 |
| aacaaggctt tgatgaagtt gcactacgcc gacttaaccg acgcttcttc cttgagacgt | 300 |
| tggattgatg ttatcaaacc agacgaagtt tacaacttgg ctgcccaatc tcacgttgct | 360 |
| gtttctttcg aaattccaga ctacactgct gacgttgtcg ctacaggcgc tttgagattg | 420 |
| ctagaagccg tcagatccca cactattgat tctggtagaa ctgtcaagta ctaccaagcc | 480 |
| ggttcttccg aaatgttcgg ttctaccca cctccccaat ctgaaaccac tcctttccac | 540 |
| ccaagatccc catacgctgc ctctaagtgt gctgcccact ggtacactgt caactacaga | 600 |
| gaagcctacg gtttgtttgc ttgtaacggt atcttgttca accatgaatc cccaagacgt | 660 |
| ggtgaaaaact tcgttaccag aaagataacc agagctttag gtagaatcaa ggttggtttg | 720 |
| caaactaagt tattcttggg taacttgcaa gctagtagaa ctggggttt cgctggtgac | 780 |
| tacgtggaag ctatgtggtt gatgttgcaa caagaaaagc cagacgatta cgttgtagct | 840 |
| accgaagagg gtcacaccgt tgaagagttc ctagacgtct ctttcggtta cttgggtttg | 900 |
| aactggaagg actacgtcga atcgaccaa agatacttta gaccagctga agttgacaac | 960 |
| ttacaaggtg acgcttccaa agccaaggaa gtcttgggtt ggaagccaca agtcggtttc | 1020 |
| gaaaagttgg ttaagatgat ggtcgatgaa gacttggaac tagctaagag agaaaaggtc | 1080 |
| ctagtcgatg ctggttacat ggacgccaag caacaaccat ag | 1122 |

<210> SEQ ID NO 37
<211> LENGTH: 972
<212> TYPE: DNA
<213> ORGANISM: Arabidopsis thaliana

<400> SEQUENCE: 37

| | | |
|---|---|---|
| atggctgaaa ccatcggttc tgaagttagc tctatgtccg acaagtccgc caagatattc | 60 |
| gtcgctggtc acagaggttt ggtcggttcc gctattgtca gaaagttgca agaacaaggt | 120 |
| ttcaccaacc tagttttgaa gacccacgct gaactagact tgactagaca agctgacgtt | 180 |
| gaatctttct tttcccaaga aaagccagtc tacgtcatct tggctgccgc taaggtcggt | 240 |
| ggcatccacg ccaacaatac ctacccagct gatttcattg gtgttaactt gcaaatccaa | 300 |
| acaaacgtta ttcactccgc ttacgaacac ggtgtcaaga aattgctatt cttgggttct | 360 |
| tcctgtatct acccaaagtt cgctccacaa cctatcccag aatctgcttt gttaaccgct | 420 |
| tctttggaac ctaccaacga atggtacgct atcgctaaga ttgccggtat caagacttgt | 480 |
| caagcctaca gaatccaaca cggttgggat gctatctctg gtatgccaac caatttgtac | 540 |
| ggtccaaacg acaacttcca cccagaaaac agtcacgttt gccagccct aatgagacgt | 600 |
| ttccatgaag ccaaggtcaa cggtgctgaa gaggttgtcg tgtggggtac tggttctccc | 660 |
| ttgagagagt tcttgcacgt tgacgatttg gctgacgcct gtgtcttctt gttagataga | 720 |
| tactcaggtt tggaacacgt caacatcggc tctggtcaag aagttactat tagagaatta | 780 |

```
gctgaattgg ttaaggaagt tgtcggtttc gaaggtaagt tgggttggga ctgtaccaag      840
ccagatggta ctccacgtaa gttgatggac tcttccaaat tggcttcctt aggttggact      900
ccaaaggttt ctttgagaga cggtttgtct caaacttacg actggtactt aaagaacgtt      960
tgcaacagat ag                                                         972
```

```
<210> SEQ ID NO 38
<211> LENGTH: 60
<212> TYPE: DNA
<213> ORGANISM: artificial sequence
<220> FEATURE:
<223> OTHER INFORMATION: H11 primer

<400> SEQUENCE: 38
ataaccataa ccaagtaata catattcaaa tggctgaaac catcggttct gaagttagct      60
```

```
<210> SEQ ID NO 39
<211> LENGTH: 60
<212> TYPE: DNA
<213> ORGANISM: artificial sequence
<220> FEATURE:
<223> OTHER INFORMATION: H12 primer

<400> SEQUENCE: 39
atgcaagatt taaagtaaat tcacggccct gcaggctatc tgttgcaaac gttctttaag      60
```

```
<210> SEQ ID NO 40
<211> LENGTH: 60
<212> TYPE: DNA
<213> ORGANISM: artificial sequence
<220> FEATURE:
<223> OTHER INFORMATION: H13 primer

<400> SEQUENCE: 40
cgcaaaataa cacagtcaaa tcaatcaaaa tggcttctga aacaatggt tctagatccg       60
```

```
<210> SEQ ID NO 41
<211> LENGTH: 60
<212> TYPE: DNA
<213> ORGANISM: artificial sequence
<220> FEATURE:
<223> OTHER INFORMATION: H14 primer

<400> SEQUENCE: 41
atcataaatc ataagaaatt cgcttactcc tatggttgtt gcttggcgtc catgtaacca     60
```

```
<210> SEQ ID NO 42
<211> LENGTH: 920
<212> TYPE: DNA
<213> ORGANISM: artificial sequence
<220> FEATURE:
<223> OTHER INFORMATION: coding sequence for a FutC enzyme from
      Helicobacter pylori with BsaI sites on ends

<400> SEQUENCE: 42
ggtctcaagg tatggctttc aaggttgttc aaatctgtgg tggtttgggc aaccaaatgt      60
tccaatacgc tttcgccaaa tctttgcaaa agcacctaaa cacccccagtt ttgttggata    120 tcacctcttt cgactggtcc aacagaaaga tgcaattgga attgttccca atcgacttac    180
catacgcttc tgccaaggaa attgctatcg ccaaaatgca acacttacca agttggtca     240 gagatacctt aaagtgtatg ggtttcgaca gagtttccca agaaattgtc ttcgagtacg    300
aaccaggttt gctaaagcct tccagattga cctactttta cggttacttc aagacccaa    360
```

```
gatacttcga tgctatttcc ccattgatca agcaaacttt caccttgcca cctcccgaaa    420
atggcaacaa caagaagaaa gaagaagaat accacagaaa gttggctcta atcttagccg    480
ctaagaactc tgttttcgtc cacgtcagac gtggcgacta cgttggtatt ggctgtcaat    540
tgggtatcga ctaccaaaag aaggctttgg aatacattgc caagagagtc ccaaacatgg    600
aactatttgt tttctgcgaa gacttgaagt tcactcaaaa cttggacttg ggttacccat    660
tcatggatat gactacaaga gacaaggaag aagaggctta ctgggatatg ttgttaatgc    720
aatcttgcaa gcacggtatc atcgccaact ccacttactc ttggtgggcc gcttacttga    780
tcaacaatcc agaaaagatc atcattggtc aaagcattg gttgttcggt cacgaaaaca    840
ttttgtgcaa agaatgggtc aagatcgagt ctcacttcga agtcaagtct aagaagtaca    900
acgcctagtc tagagagacc                                                920
```

<210> SEQ ID NO 43
<211> LENGTH: 45
<212> TYPE: DNA
<213> ORGANISM: artificial sequence
<220> FEATURE:
<223> OTHER INFORMATION: H305 primer

<400> SEQUENCE: 43

```
aattcggtcg aaaaaagaaa aggaggcaga ttgtactgag agtgc                     45
```

<210> SEQ ID NO 44
<211> LENGTH: 45
<212> TYPE: DNA
<213> ORGANISM: artificial sequence
<220> FEATURE:
<223> OTHER INFORMATION: H306 primer

<400> SEQUENCE: 44

```
caggcaagtg cacaaacaat acttagtgcg gtatttcaca ccgca                     45
```

<210> SEQ ID NO 45
<211> LENGTH: 20
<212> TYPE: DNA
<213> ORGANISM: artificial sequence
<220> FEATURE:
<223> OTHER INFORMATION: H291 primer

<400> SEQUENCE: 45

```
gccagaggtc aagccagaag                                                 20
```

<210> SEQ ID NO 46
<211> LENGTH: 20
<212> TYPE: DNA
<213> ORGANISM: artificial sequence
<220> FEATURE:
<223> OTHER INFORMATION: H292 primer

<400> SEQUENCE: 46

```
ccgttgtcgt cgttcttcaa                                                 20
```

INCREASING ACTIVITY OF 2'FUCOSYLLACTOSE TRANSPORTERS ENDOGENOUS TO MICROBIAL CELLS

INCORPORATION BY REFERENCE OF THE SEQUENCE LISTING

The sequence listing provided in the file named "NB06492USNP_SequenceListing_ST25" with a size of 50,104 bytes which was created on Apr. 19, 2018 and which is filed herewith, is incorporated by reference herein in its entirety.

FIELD

The disclosure relates to the modification of growth conditions and genetic engineering of microbial cells to increase the activity of endogenous transporters of 2' fucosyllactose.

BACKGROUND

2' fucosyllactose (2'FL) is a human milk oligosaccharide (HMO) shown to be beneficial to infant health. E. coli has been genetically engineered to produce 2'FL by introducing a biosynthetic pathway to GDP-L-fucose, which is then combined with lactose by catalytic action of an □-1,2-fucosyltransferase to generate 2'FL (Lee et al. (2012) Microb. Cell Factories 11, 48-57; Baumgartner et al. (2013) 12, 40-53; US Patent Application 20140024820). U.S. Pat. No. 8,652,808 discloses a bacterial cell engineered to synthesize 2'FL and a sugar efflux transporter to excrete it to the medium. In addition, others have established a metabolic route to GDP-fucose in Corynebacterium glutamicum that could enable production of 2'FL or other fucosylated HMOs (Chin et al (2013) Bioprocess Biosyst. Eng 36, 749-756).

A metabolic route to GDP-fucose has been established in Saccharomyces cerevisiae (Matila et al. (2000) Glycobiology 10, 1041-1047)), and the synthesis of 2'FL in Kluyveromyces lactis has been reported as a method to demonstrate successful synthesis of GDP-fucose (US Patent Application 20100120701). However, Applicants are unaware of a reported method for increasing the endogenous activity of a 2'FL transporter in microbial cells.

SUMMARY

In one aspect, the disclosure provides a fermentation broth which includes a microbial cell having increased export of 2' fucosyllactose, the microbial cell having been subjected to a condition under which the activity of an endogenous transporter is increased relative to the activity of the endogenous transporter in the microbial cell in the absence of subjecting the microbial cell to the condition.

In another aspect, the disclosure provides a method for increasing the export of 2' fucosyllactose from a microbial cell. The method includes the steps of a) obtaining a 2'FL-containing microbial cell and b) subjecting the microbial cell to a condition under which the activity of an endogenous transporter is increased relative to the activity of the endogenous transporter in the microbial cell in the absence of subjecting the microbial cell to the condition.

In a further aspect, the disclosure provides a method for identifying an endogenous yeast transporter for exporting 2' fucosyllactose from a yeast cell. The method includes the steps of a) obtaining a 2'FL-containing yeast cell and b) subjecting the yeast cell to a condition under which the export of 2'FL is increased relative to the export of 2'FL in the yeast cell in the absence of subjecting the yeast cell to the condition. The method further includes the step of identifying an endogenous yeast transporter with increased activity in the yeast cell as an endogenous yeast transporter for exporting 2' fucosyllactose.

In yet a further aspect, the disclosure provides a genetically engineered microbial cell. The genetically engineered microbial cell includes a genetic modification which increases the activity of one or more endogenous transporters whereby export of 2' fucosyllactose from the microbial cell is increased.

BRIEF DESCRIPTION OF THE DRAWINGS AND SEQUENCE DESCRIPTIONS

Figure 1:
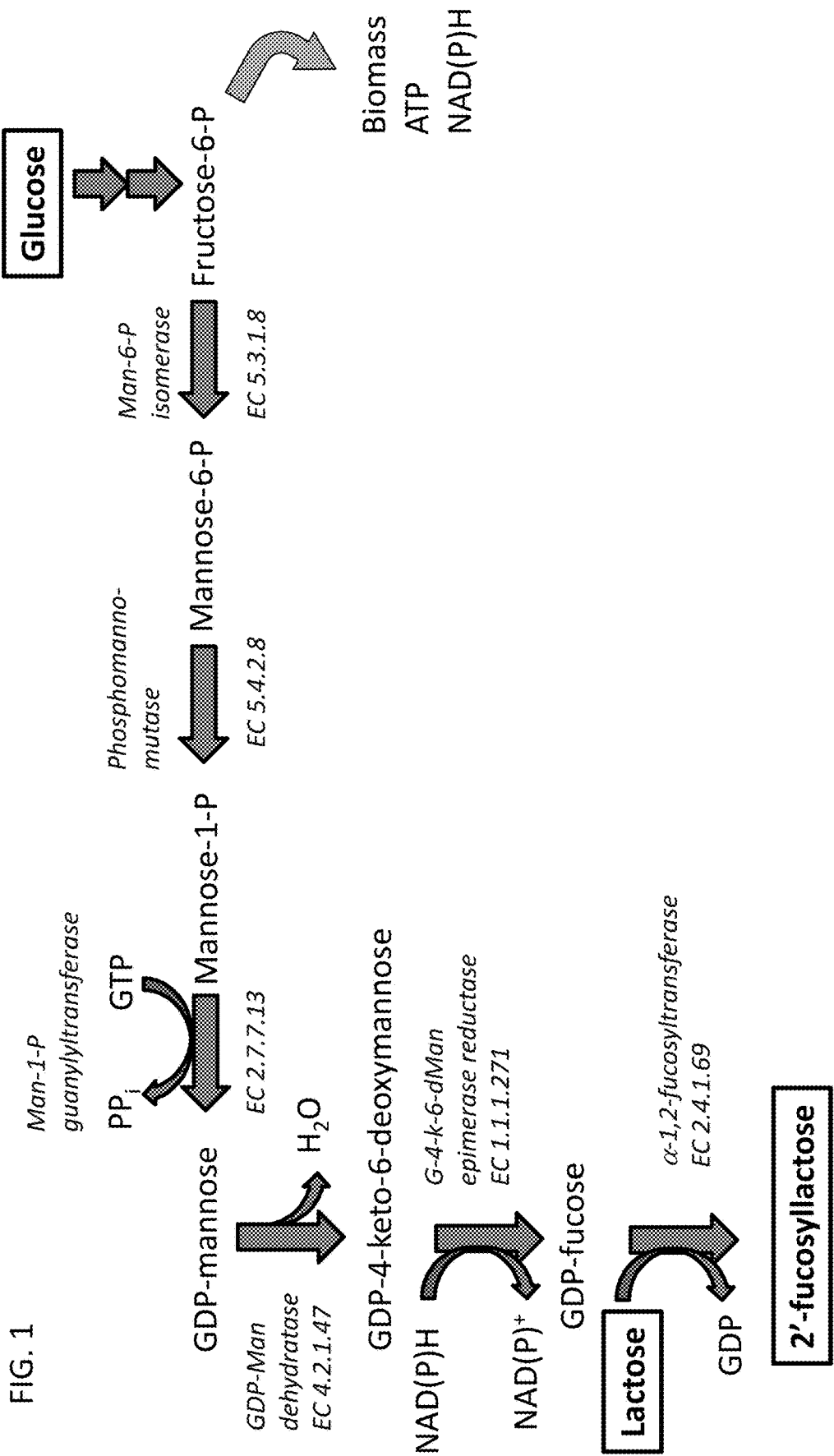
FIG. 1 shows a diagram of a biosynthetic pathway for production of 2-FL.

The disclosure can be more fully understood from the following detailed description and the accompanying sequence descriptions which form a part of this application.

The following sequences conform with 37 C.F.R. 1.821-1.825 ("Requirements for Patent Applications Containing Nucleotide Sequences and/or Amino Acid Sequence Disclosures—the Sequence Rules") and are consistent with World Intellectual Property Organization (WIPO) Standard ST.25 (2009) and the sequence listing requirements of the EPO and PCT (Rules 5.2 and 49.5(a-bis), and Section 208 and Annex C of the Administrative Instructions). The symbols and format used for nucleotide and amino acid sequence data comply with the rules set forth in 37 C.F.R. § 1.822.

SEQ ID NO:1 is the nucleotide sequence of the coding region for lactose permease from Kluyveromyces lactis.

SEQ ID NOs:2, 3, 5, 6, 8, 9, 11-15, 19-22, 28-31, 38-41, and 43-46 are PCR and/or sequencing primers.

SEQ ID NO:4 is the nucleotide sequence of the PMA1 promoter.

SEQ ID NO:7 is the nucleotide sequence of the TPS1 terminator.

SEQ ID NO:10 is the nucleotide sequence of plasmid pUC19-URA3-YPRCA15.

SEQ ID NO:17 is the nucleotide sequence of a Kluyveromyces lactis beta-galactosidase 5' fragment.

SEQ ID NO:18 is the nucleotide sequence of a Kluyveromyces lactis beta-galactosidase 3' fragment.

SEQ ID NO:23 is the nucleotide sequence of plasmid pHR81-ILV5p-R8B2y2.

SEQ ID NO:24 is the nucleotide sequence of the ILV5 promoter.

SEQ ID NO:25 is the nucleotide sequence of the ILV5 terminator.

SEQ ID NO:26 is the nucleotide sequence of the coding region for GDP-mannose dehydratase from E. coli.

SEQ ID NO:27 is the nucleotide sequence of the coding region for GDP-4-keto-6-deoxymannose epimerase reductase from E. coli.

SEQ ID NO:32 is the nucleotide sequence of the PDC1 promoter.

SEQ ID NO:33 is the nucleotide sequence of the ADH1 terminator.

SEQ ID NO:34 is the nucleotide sequence of the hybrid promoter (PGK1(UAS)-FBA1).

SEQ ID NO:35 is the nucleotide sequence of the TDH3 terminator.

SEQ ID NO: 36 is the nucleotide sequence of the coding region for GDP-mannose dehydratase from *A. thaliana*.

SEQ ID NO: 37 is the nucleotide sequence of the coding region for GDP-4-keto-6-deoxymannose epimerase reductase from *A. thaliana*.

SEQ ID NO:42 is the nucleotide sequence of the coding region for FutC from *Helicobacter pylori* with BsaI sites on the ends.

SEQ ID NO:16 is the nucleotide sequence of the coding region for beta-galactosidase from *Kluyveromyces* lactis.

DETAILED DESCRIPTION

The following definitions may be used for the interpretation of the claims and specification:

As used herein, the terms "comprises." "comprising," "includes," "including," "has," "having." "contains" or "containing," or any other variation thereof, are intended to cover a non-exclusive inclusion. For example, a composition, a mixture, process, method, article, or apparatus that comprises a list of elements is not necessarily limited to only those elements but may include other elements not expressly listed or inherent to such composition, mixture, process, method, article, or apparatus. The compositions and methods disclosed herein may comprise, consist, or consist essentially of any element disclosed herein. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, the indefinite articles "a" and "an" preceding an element or component of the invention are intended to be nonrestrictive regarding the number of instances (i.e. occurrences) of the element or component. Therefore "a" or "an" should be read to include one or at least one, and the singular word form of the element or component also includes the plural unless the number is obviously meant to be singular.

The term "invention" or "present invention" as used herein is a non-limiting term and is not intended to refer to any single embodiment of the particular invention but encompasses all possible embodiments as described in the specification and the claims.

As used herein, the term "about" modifying the quantity of an ingredient or reactant of the invention employed refers to variation in the numerical quantity that can occur, for example, through typical measuring and liquid handling procedures used for making concentrates or use solutions in the real world; through inadvertent error in these procedures: through differences in the manufacture, source, or purity of the ingredients employed to make the compositions or carry out the methods; and the like. The term "about" also encompasses amounts that differ due to different equilibrium conditions for a composition resulting from a particular initial mixture. Whether or not modified by the term "about", the claims include equivalents to the quantities. In one embodiment, the term "about" means within 10% of the reported numerical value, preferably within 5% of the reported numerical value.

"Gene" refers to a nucleic acid fragment that expresses a specific protein or functional RNA molecule, which may optionally include regulatory sequences preceding (5' non-coding sequences) and following (3' non-coding sequences) the coding sequence. "Native gene" or "wild type gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature.

The term "endogenous gene" refers to a native gene of an organism. A "foreign" gene refers to a gene not normally found in the host organism, but that is introduced into the host organism by gene transfer. Foreign genes can comprise native genes inserted into a non-native organism, or chimeric genes.

"Promoter" or "Initiation control regions" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. Promoters which cause a gene to be expressed in a cell type at most times are commonly referred to as "constitutive promoters".

The term "expression", as used herein, refers to the transcription and stable accumulation of coding (mRNA) or functional RNA derived from a gene. Expression may also refer to translation of mRNA into a polypeptide. "Overexpression" refers to the production of a gene product in transgenic organisms that exceeds levels of production in normal or non-transformed organisms.

The term "transformation" as used herein, refers to the transfer of a nucleic acid fragment into a host organism, resulting in genetically stable inheritance. The transferred nucleic acid may be in the form of a plasmid maintained in the host cell, or some transferred nucleic acid may be integrated into the genome of the host cell. Host organisms containing the transferred nucleic acid fragments are referred to as "transgenic" or "recombinant" or "transformed" organisms or "transformants".

The terms "plasmid" and "vector" as used herein, refer to an extra chromosomal element often carrying genes which are not part of the central metabolism of the cell, and usually in the form of circular double-stranded DNA molecules. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell.

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "selectable marker" means an identifying factor, usually an antibiotic or chemical resistance gene, that is able to be selected for based upon the marker gene's effect, i.e., resistance to an antibiotic, wherein the effect is used to track the inheritance of a nucleic acid of interest and/or to identify a cell or organism that has inherited the nucleic acid of interest.

As used herein the term "codon degeneracy" refers to the nature of the genetic code permitting variation of the nucleotide sequence without affecting the amino acid sequence of an encoded polypeptide. The skilled artisan is well aware of the "codon-bias" exhibited by a specific host cell in usage of nucleotide codons to specify a given amino acid. Therefore, when synthesizing a gene for improved expression in a host cell, it may be desirable to design the gene such that its frequency of codon usage approaches the frequency of preferred codon usage of the host cell.

The term "codon-optimized" as it refers to genes or coding regions of nucleic acid molecules for transformation of various hosts, refers to the alteration of codons in the gene or coding regions of the nucleic acid molecules to improve the production of the polypeptide encoded by the DNA without altering the sequence of the polypeptide.

The term "heterologous" means not naturally found in the cellular location of interest. For example, a heterologous gene refers to a gene that is not naturally found in the host organism, but that is introduced into the host organism by gene transfer. For example, a heterologous nucleic acid molecule that is present in a chimeric gene is a nucleic acid molecule that is not naturally found associated with the other segments of the chimeric gene, such as the nucleic acid molecules having the coding region and promoter segments not naturally being associated with each other.

As used herein, an "isolated nucleic acid molecule" is a polymer of RNA or DNA that is single- or double-stranded, optionally containing synthetic, non-natural or altered nucleotide bases. An isolated nucleic acid molecule in the form of a polymer of DNA may be comprised of one or more segments of cDNA, genomic DNA or synthetic DNA.

Standard recombinant DNA and molecular cloning techniques used herein are well known in the art and are described by Sambrook, J. and Russell, D., *Molecular Cloning: A Laboratory Manual*, Third Edition, Cold Spring Harbor Laboratory Press, Cold Spring Harbor, NY (2001); and by Silhavy, T. J., Bennan, M. L. and Enquist, L. W., *Experiments with Gene Fusions*, Cold Spring Harbor Laboratory Press, Cold Spring Harbor, NY (1984): and by Ausubel, F. M. et. al., *Short Protocols in Molecular Biology*, 5$^{th}$ Ed. Current Protocols. John Wiley and Sons, Inc., N.Y., 2002. Additional methods used here are in Methods in Enzymology, Volume 194, Guide to Yeast Genetics and Molecular and Cell Biology (Part A, 2004, Christine Guthrie and Gerald R. Fink (Eds.), Elsevier Academic Press, San Diego, CA).

In one aspect, the disclosure provides a fermentation broth which includes a microbial cell having increased export of 2' fucosyllactose, the microbial cell having been subjected to a condition under which the activity of an endogenous transporter is increased relative to the activity of the endogenous transporter in the microbial cell in the absence of subjecting the microbial cell to the condition.

The fermentation broth can be any fermentation broth in which microbial cells can be fermented such as those known in the art. A fermentation broth will typically contain suitable carbon substrates, most typically glucose, but may contain other carbon sources, such as the non-fermentable carbon sources disclosed below. Carbon substrates may be provided by glucose preparations or by glucose and other sugars prepared from starch biomass or lignocellulosic biomass. A starch biomass, such as ground corn grain, is typically treated using alpha amylase and glucoamylase enzymes to prepare a hydrolyzed mash that can be used as fermentation medium. A lignocellulosic biomass is typically pretreated with mechanical energy and chemicals, then hydrolyzed using multiple glycosidases including cellulases and other enzymes, such as disclosed in WO 2011/038019, to produce a lignocellulosic biomass hydrolysate containing glucose, xylose, and arabinose that can be used as fermentation medium, for example as disclosed in U.S. Pat. No. 7,932,063. In certain embodiments, the fermentation broth includes one or more non-fermentable carbon sources such as ethanol, glycerol, and acetate. The fermentation broth may include these non-fermentable carbon sources in addition to or in place of fermentable carbon sources like glucose.

Specific attributes of the fermentation broth and fermentation conditions will be determined by the type of microbial cell used. One of skill in the art will be familiar with conditions such as pH, oxygenation, and temperature used for various bacterial and fungal cells.

In certain embodiments, the condition for increasing activity of an endogenous transporter in the microbial cell is a growth condition. In certain embodiments, the growth condition is a condition involving the components of the medium in which the microbial cell is grown, such as components of the fermentation broth. In specific embodiments, increased activity of an endogenous transporter is obtained by growing the microbial cell in a medium which has one or more of the following characteristics: the medium includes amino acids, the medium is a glucose limited medium, and the medium includes ethanol. Media with these characteristics can be made by methods known in the art, such as the exemplary media described in Example 3. In a specific embodiment, the medium includes amino acids and at least one of folic acid, riboflavin, micronutrients, and adenine. In a particularly specific embodiment, the medium is the synthetic complete medium described in Example 3. Where the endogenous transporter is a transporter capable of exporting 2' fucosyllactose from the microbial cell, increased activity of the transporter would, in turn, result in increased export of 2' fucosyllactose present in the microbial cell. Therefore, by subjecting the microbial cell to the condition, a microbial cell, as present in the fermentation broth, with increased export of 2' fucosyllactose is obtained.

In that regard, in another aspect, the disclosure provides a method of increasing export of 2' fucosyllactose from a microbial cell. The method includes the steps of a) obtaining a 2'FL-containing microbial cell and b) subjecting the microbial cell to a condition under which the activity of an endogenous transporter is increased relative to the activity of the endogenous transporter in the microbial cell in the absence of subjecting the microbial cell to the condition.

The microbial cell can be any microbial cell from which 2' fucosyllactose can be exported. In certain embodiments, the microbial cell is a bacterial cell or a fungal cell. In particular embodiments, the bacterial cell is of the genus such *Escherichia, Bacillus, Methylomonas, Pseudomonas, Lactobacillus,* or *Corynebacterium*. In various embodiments the microbial cell is an *Escherichia coli* or *Bacillus subtilis* cell. In certain embodiments, the microbial cell is a yeast cell. In certain embodiments, the yeast cell is of the genus Saccharomyces, Yarrowia, Kluyveromyces, Candida, Hansenula, Pichia, Schizosaccharomyces, Zygosaccharomyces, Debaryomyces, Brettanomyces, Pachysolen, Issatchenkia, Trichosporon, or Yamadazyma. In various embodiments the yeast cell is from Saccharomyces cerevisiae, Yarrowia lipolytica or Kluyveromyces lactis.

In certain embodiments, the microbial cell is a cell that is genetically engineered to produce 2'FL, i.e., is a 2'FL-producing cell. Methods for genetically engineering E. coli cells to produce 2'FL have been previously described (Lee et al. (2012) Microb. Cell Factories 11, 48-57; Baumgartner et al. (2013) 12, 40-53: US Patent Application 20140024820). Methods for genetically engineering yeast cells, such as yeasts of the genera Saccharomyces, Yarrowia Kluyveromyces, Pichia, and Hansenula, to produce 2'FL are disclosed herein. In certain embodiments, yeast cells capable of producing 2'FL are constructed as described in Example 1. Specifically, the Example discloses a method in which 2'FL producing yeast cells are made by expressing heterologous coding regions for GDP-mannose-4,6-dehydratase (GMD; EC 4.2.1.47), GDP-4-keto-6-D-deoxymannose epimerase-reductase (GDP-L-fucose synthase; GMER: EC 1.1.1.271), and 2-N-L-fucosyltransferase (2FT; EC 2.4.1.69) in a yeast host that has a native pathway to GDP-mannose, and then supplying a source of lactose for the 2FT reaction. The native yeast pathway to GDP-mannose optionally may be enhanced by increasing expression of the endogenous pathway enzymes using methods described below. This pathway is shown in FIG. 1.

As shown in FIG. 1, one method of producing 2'FL uses an a-1,2-fucosyltransferase to catalyze the combination of lactose and GDP-fucose. In certain embodiments, it is expected that increasing the ability of a microbial cell to import lactose will result in increased 2'FL within the microbial cell resulting in greater 2'FL available for export. In certain embodiments, in addition to being genetically engineered to express the pathway enzymes for 2'FL production, the microbial cell is genetically engineered to include a nucleic acid sequence which codes for a lactose transporter. The lactose transporter can be any lactose transporter known in the art that can be expressed in the microbial cell such as the lactose transporter encoded by SEQ ID NO: 1.

The fermentation broth may contain additional substrates that contribute to production of the desired product. For example, where the microbial cell is a 2'FL-producing cell, the broth may contain lactose which can facilitate the production of fucosyllactose (see FIG. 1). Typically, these substrates would be provided by a batch feeding process as is known in the art.

2'FL-producing yeast cells are constructed according to methods well-known to one skilled in the art. Expression of heterologous coding regions in a host cell is known to one of skill in the art. The coding region for the desired polypeptide is readily obtained from the genome of the cell in which it is natively expressed, as well known to one skilled in the art. In addition, coding regions may be synthesized using codon optimization for the target host cell. Typically the nucleotide sequence encoding the amino acid sequence of the enzyme with desired activity is operably linked in a chimeric gene (or expression cassette) to a promoter that is active in the target host cell. Typically a transcription terminator is linked at the 3' end of the coding region. For example, for expression in a yeast cell a number of yeast promoters can be used in constructing chimeric genes encoding a desired enzyme, including, but not limited to constitutive promoters FBA1, GPD1, ADH1, GPM, TPI1, TDH3, PGK1, Ilv5, and the inducible promoters GAL1, GAL10, and CUP1. Suitable transcription terminators include, but are not limited to FBAt, GPDt, GPMt, ERG10t, GAL1t, CYC1t, ADH1t, TAL1t, TKL1t, ILV5t, and ADHt.

A chimeric gene for host cell expression is typically constructed in or transferred to a vector for further manipulations. The vector used is determined by the target host cell, and the transformation and/or integration methods to be used. Vectors for a target host cell are well known in the art. For example, for yeast expression chimeric genes may be cloned into E. coli-yeast shuttle vectors, and transformed into yeast cells. These vectors allow propagation in both E. coli and yeast cells. Typically the vector contains a selectable marker and sequences allowing autonomous replication or chromosomal integration in the desired host. Plasmids for DNA integration may include transposons, regions of nucleic acid sequence homologous to the target genome, or other sequences supporting integration. It is well known how to choose an appropriate vector for the desired target host and the desired function. In addition, a selectable marker used to obtain transformed cells may be bounded by site-specific recombination sites, so that after expression of the corresponding site-specific recombinase, the resistance gene is excised from the genome. Multiple copies of gene may be introduced on a plasmid or integrated into the cell genome.

There are many tests to determine if a microbial cell has increased export of 2'FL. For example, the export of 2'FL from a strain that synthesizes it (i.e., a 2'FL-producing cell) can be measured by detecting it in the broth of fermentations under conditions in which the 2'FL is being synthesized inside the cell. The 2'FL can be detected directly by means of chromatography of clarified broth samples removed from the fermentation, followed by detection by, for example, evaporative light scattering detection. The 2'FL can also be detected in clarified broth samples indirectly by means of a coupled enzyme assay, first catalyzing hydrolysis of the 2'FL with an □-1,2-L-fucosidase enzyme (EC 3.2.1.63) and then catalyzing oxidization of the resulting fucose to fuconate with an $NAD^*$-dependent L-fucose dehydrogenase enzyme (EC 1.1.1.122), and detecting the product NADH spectrophotometrically. 2'FL export may be measured indirectly based on a change in pH if the heterologous nucleic acid sequence encodes a protein which moves H+ during 2'FL export. The use of antibodies to detect products of fermentation reactions by ELISA-type assays are well known in the art, as is the analogous use of RNA-aptamers specific for the desired product. Higher throughput screens could be available by screening the growth rates of strains engineered to make 2'FL with different heterologous nucleic acid sequences, as it is to be expected that buildup of an osmolyte such as 2'FL will cause stress that will inhibit cell growth, or that buildup of pathway intermediates will be otherwise deleterious to cell growth.

The above-described methods for detecting 2' fucosyllactose can be used to identify microbial cells having increased export of 2' fucosyllactose. Microbial cells having increased export of 2' fucosyllactose can be identified by determining an amount of 2' fucosyllactose present in a fermentation broth of a first microbial cell subjected to a condition, such as the growth conditions described above for increasing 2' fucosyllactose export. The amount of 2' fucosyllactose in the fermentation broth can then be compared to an amount of 2' fucosyllactose in the fermentation broth of a second microbial cell that was not subjected to the growth condition. In certain embodiments, the first and second microbial cells are the same cell, e.g., where the amount of 2' fucosyllactose is measured at different time points, e.g., prior to and after subjecting the microbial cell to the condition. In certain embodiments, the first and second microbial cells are different cells. Where the microbial cells are different cells, the microbial cells will be microbial cells of the same genus and species, and, in particular embodiments, will be derived from the same parental strain. The comparison of the amount of 2' fucosyllactose in the fermentation broths for the first and second cells can be carried out on an absolute basis, e.g., based on the absolute concentration of 2' fucosyllactose in the fermentation broths, or on a relative basis. A relative analysis can be carried out by measuring an amount of 2' fucosyllactose in the fermentation broths of the first and second microbial cells relative to the amounts of 2' fucosyllactose in the first and second cells. When using a relative analysis, a microbial cell having increased 2' fucosyllactose export can be identified as a cell with a greater relative concentration of 2' fucosyllactose in the fermentation broth to the concentration of 2' fucosyllactose in the cell. This can be done, for example, by calculating a percentage or ratio of the amount of 2' fucosyllactose in the fermentation broth for each of the first and second cells relative to the corresponding cellular concentrations and identifying the cell associated with a fermentation broth having a greater percentage or ratio of 2' fucosyllactose. In certain embodiments, the cell having increased export of 2'FL has increased export of 2'FL relative to another cell that also exports 2'FL. In certain embodiments, the cell having increased export of 2'FL has increased export of 2'FL relative to another cell that does not export 2'FL. Microbial cells having increased export of 2' fucosyllactose can, in turn, be used to identify endogenous transporters of 2' fucosyllactose.

In that regard, a further aspect of the disclosure relates to a method of identifying an endogenous yeast transporter for exporting 2' fucosyllactose from a yeast cell. The method includes the steps of a) obtaining a 2'FL-containing yeast cell and b) subjecting the yeast cell to a condition under which the export of 2'FL is increased relative to the export of 2'FL in the yeast cell in the absence of subjecting the yeast cell to the condition. The method further includes the step of identifying an endogenous yeast transporter with increased activity in the yeast cell as an endogenous yeast transporter for exporting 2' fucosyllactose.

The yeast cell can be any yeast cell that contains 2'FL, including a yeast cell from any yeast disclosed herein. The condition to which the yeast cell is subjected can be any condition which results in an increase in 2'FL export, including any growth condition disclosed herein. Yeast cells having increased export of 2'FL can then be used to identify endogenous yeast transporters for 2'FL export by identifying endogenous yeast transporters having increased activity in the yeast cells with increased 2'FL export. Endogenous transporters for 2'FL export can be identified by any method known in the art. One such method would be to conduct RNA transcript analysis by one of a variety of techniques, including RNASeq, to look for genes whose transcription is enhanced in a yeast cell where 2'FL export is increased relative to the transcription of the genes in a comparison cell. Another approach is to conduct an analogous proteomics experiment to determine proteins whose biosynthesis is enhanced in a yeast cell where 2'FL export is increased. Those proteins whose genes show enhanced RNA translation in cells with increased export of 2'FL or whose biosynthesis is enhanced in cells having increased export of 2'FL are candidates for endogenous yeast 2'FL transporters. Identified RNA transcripts or proteins with increased activity may be filtered by, for example, analyzing their sequences for similarity to membrane proteins, including known transporters. Once endogenous yeast transporters for 2'FL are identified, yeast cells can be genetically modified to increase the activity of the transporters.

In that regard, in a further aspect, the disclosure provides a genetically engineered microbial cell comprising a genetic modification which increases the activity of one or more endogenous transporters. The activity of the one or more endogenous transporters is increased such that export of 2'FL from the microbial cell is increased.

The genetically engineered microbial cell can be any microbial cell that can be genetically engineered with an increased activity in an endogenous transporter such that export of 2'FL from the microbial cell is increased. Such cells, include, but are not limited to, any bacterial or fungal cell disclosed herein, including any yeast cell disclosed herein. The microbial cell that is genetically engineered to increase the activity of the endogenous transporter may contain further genetic modifications, including, but not limited to, genetic modifications which introduce one or more pathway genes for the production of 2'FL, such as the pathway genes disclosed herein.

The genetic modification which increases the activity of one or more endogenous transporters can increase the activity of any endogenous microbial transporter for 2'FL. In certain embodiments, the genetic modification increases the activity of an endogenous transporter identified by a method for identifying endogenous 2'FL transporters disclosed herein.

Increased activity of an endogenous gene may be achieved by any method known in the art. Methods that are typically known to one skilled in the art include, for example, replacing the promoter of the endogenous gene with a more highly active promoter, replacing the terminator with one that allows greater translation, introducing a chimeric gene encoding the protein encoded by the endogenous gene into the cell on a multi-copy plasmid, introducing a chimeric gene encoding the protein encoded by the endogenous gene into the cell where the promoter of the chimeric gene is of high activity, and/or integrating multiple copies of the endogenous gene and/or of one or more chimeric genes for expression of the coding region of the endogenous gene. In addition, a chimeric gene containing a heterologous coding region for a protein having the same activity as the endogenous gene may be introduced into the microbial cell.

In various embodiments, further genetic engineering modifications are made to the microbial cell to improve the efficiency of production of 2'FL. In certain embodiments, modifications are made to improve carbon flow through the introduced pathway for 2'FL production which may include, but are not limited to, knocking out pathways that compete for key intermediates of the 2'FL pathway and/or redirecting reducing equivalents to the 2'FL pathway.

2'FL exported from a microbial cell as disclosed herein can be isolated from fermentation broth and used in various food products, such as nutritional supplements. For example, the 2'FL can be added to formula for infants, toddlers, or children.

EXAMPLES

The disclosure is further defined in the following Examples. It should be understood that these Examples, while indicating preferred embodiments, are given by way of illustration only. From the above discussion and these Examples, one skilled in the art can ascertain the characteristics of this disclosure, and without departing from the spirit and scope thereof, can make various changes and modifications to adapt the disclosure to various uses and conditions.

General Methods

The meaning of abbreviations is as follows: "kb" means kilobase(s), "bp" means base pairs, "nt" means nucleotide(s), "hr" means hour(s), "min" means minute(s), "sec" means second(s), "d" means day(s), "L" means liter(s). "ml" or "mL" means milliliter(s), "□L" means microliter(s), "□g" means microgram(s), "ng" means nanogram(s), "mg" means milligram(s), "mM" means millimolar, "□M" means micromolar. "nm" means nanometer(s), "□mol" means micromole(s), "pmol" means picomole(s), Standard recombinant DNA and molecular cloning techniques used here are well known in the art and are described by Sambrook, J., Fritsch, E. F. and Maniatis, T., Molecular Cloning: A Laboratory Manual, $2^{nd}$ ed., Cold Spring Harbor Laboratory: Cold Spring Harbor, NY (1989) (hereinafter "Maniatis"); and by Silhavy, T. J., Bennan, M. L. and Enquist, L. W., Experiments with Gene Fusions, Cold Spring Harbor Laboratory: Cold Spring Harbor, NY (1984); and by Ausubel, F. M. et al., Current Protocols in Molecular Biology, published by Greene Publishing Assoc. and Wiley-Interscience, Hoboken, NJ (1987), and by Methods in Yeast Genetics, 2005, Cold Spring Harbor Laboratory Press, Cold Spring Harbor, NY General Methods Transformation of Saccharomyces cerevisiae Strains Saccharomyces cerevisiae strains are made competent for transformation via protocols employing lithium acetate and polyethylene glycol (described in Amberg, D. C., Burke, D. J. and Strathern, J. N. Methods in Yeast Genetics: A Cold Spring Harbor Laboratory Course Manual, Cold Spring Harbor Press, 2005). In most cases, a commercial kit is used (e.g. Frozen EZ Yeast Transformation II Kit™, Zymo™ Research, Irvine, Calif.), though for some lineages a higher efficiency method such as that by Gietz et al. (1992, Nucleic Acids Res. 20(6): 1425) with extension of 42° C. incubation to 40 minutes is used for chromosomal integrations. Integration events are confirmed by PCR. Yeast cells from colonies or patches are introduced directly into PCR reaction mixtures (e.g. JumpStart™ REDTaq® ReadyMix™) or pretreated with the chelation resin Chelex® resin (BioRad, Hercules, Calif.) prior to PCR as follows. A sterile toothpick is used to transfer approximately one cubic millimeter of cells to 100 µl of 5% Chelex® (w/v) suspended in ddH2O in a 0.2 ml PCR tube. Tubes are incubated at 99° C. for 10 min followed centrifugation for 3 min at 14000 rpm to pellet all cellular debris at the bottom of the tube.

Example 1

Construction of the 2'fucosyllactose-Producing Saccharomyces cerevisiae Strain HS0007

Integration of Lactose Permease GeneA nucleic acid molecule having the coding sequence for the lactose permease from Kluyveromyces lactis (LAC12) was obtained from a commercial gene synthesis company (IDT™, Coralville, Iowa)(SEQ ID No:1). The linear fragment was cloned into pCRII-Blunt™ (TOPO™) vector (Zero Blunt™ TOPO™ cloning vector, Invitrogen™) per the manufacturer's instructions. Clones were sequenced. The LAC12 coding region was PCR amplified using primers H89 and H94 (SEQ ID NOs:2 and 3), and this nucleic acid fragment was joined to promoter and terminator sequences using PCR. The PMA1 promoter (SEQ ID NO:4) was amplified from S. cerevisiae genomic DNA using primers H92 and H93 (SEQ ID NOs:5 and 6). The TPS1 terminator (SEQ ID NO:7) was amplified from S. cerevisiae genomic DNA using primers H90 and H91 (SEQ ID NOs:8 and 9). The fused promoter, coding region and terminator were amplified with H91 and H92 primers, digested with BamHI and PmeI, and cloned into pUC19-URA3-YPRCΔ15 (SEQ ID NO:10; described in US Patent Application Publication No. 20130203138, which is incorporated herein by reference for the disclosure of the construction of the plasmid), previously digested with BamHI and PmeI. Ligation mixtures were transformed into E. coli Stbl3 cells (Life Technologies™). Colonies arising with ampicillin selection (100 µg/mL) were screened by PCR to confirm the LAC12 clones. Positive clones were sequenced. A clone containing a confirmed sequence was linearized with SphI and transformed into strain PNY1500 (also called BP857; described in U.S. Pat. No. 8,871,488) which is a ura34 his34 variant of CEN.PK 113-7D. Cells were plated on synthetic complete medium without uracil. Colonies were screened for the expected integration event using primers BK1042 and H95 for the 5' end (SEQ ID NOs: 11 and 12), and BK1043 and 92 for the 3' end, (SEQ ID NOs:13 and 14). Two clones were selected for marker recycling, as follows. Clones were grown overnight in yeast extract-peptone-dextrose (YPD) medium, and then streaked onto synthetic complete medium containing 0.1% 5-fluoroorotic acid (5-FOA). Colonies were patched to synthetic complete medium without uracil to confirm lack of growth without uracil (i.e. loss of the URA3 auxotrophic marker). Uracil auxotrophic clones were evaluated by PCR (using primers BK1043 and H96, SEQ ID NO:15) to confirm that the URA3 marker was removed via homologous recombination. Multiple clones were tested for lactose consumption upon transformation with the pHR81-LAC4 plasmid described below. One clone that was able to grow on lactose was designated HS0003.

Beta-galactosidase is temporarily expressed to test for lactose permease activity. The coding sequence for beta-galactosidase from Kluyveromyces lactis (SEQ ID NO:16) was obtained from a commercial gene synthesis company (IDT, Coralville, Iowa). Due to its size, the coding sequence was ordered in two overlapping nucleic acid fragments (5' fragment and 3'fragment: SEQ ID NOs:17 and 18, respectively). The linear fragments were each cloned into pCRII-Blunt™ (TOPO™) vector (Zero Blunt™ TOPO™ cloning vector, Invitrogen™) per the manufacturer's instructions. Clones were sequenced. One clone for each plasmid was selected and the two gene fragments were amplified by PCR with primers (H98 and M13ForTOPO for the 5' fragment and M13RevTOPO and H99 for the 3' fragment, SEQ ID NOs:19-22). An expression plasmid was assembled using gap repair cloning methodology as follows. The gene fragments were combined with PmeI digested pHR81-ILV5p-R8B2y2 (SEQ ID NO:23; described in US20130252296), which contains the ILV5 promoter and terminator (SEQ ID NOs:24 and 25), and transformed into PNY1500 yprΔ15Δ::LAC12 cells (described above). Transformants were obtained via selection on synthetic complete medium lacking uracil. Colonies were subsequently patched to medium containing lactose as the carbon source. Proper assembly of the expression plasmid (named pHR81::ILV5p-LAC4-ILV5t) was also confirmed using PCR and correlated with the ability to grow on lactose.

Construction of Plasmids Encoding GDP-Mannose Dehydratase and GDP-4-keto-6-deoxymannose Epimerase Reductase Nucleic acid molecules having the coding sequences for GDP-mannose dehydratase (GMD) and GDP-4-keto-6-deoxymannose epimerase reductase (GMER) from *E. coli* were obtained from a commercial gene synthesis company (IDT™, Coralville, Iowa) (SEQ ID NOs:26 and 27). The linear gene fragments were cloned into pCRII-Blunt™ (Zero Blunt™ TOPO™ cloning vector, Invitrogen™) per the manufacturer's instructions. Clones were sequenced. One clone for each gene was used as a PCR template to add 5' and 3' extensions to the genes to allow subsequent cloning by homologous recombination (gap repair cloning). These primers were H17 and H18 (SEQ ID NOs:28 and 29) for GMD and H15 and H16 (SEQ ID NOS:30 and 31) for GMER. The recipient vector was prepared in two fragments from pRS413::BiADH-kivD (described in WO 2014/151645; SEQ ID NO: 98 therein, which is incorporated by reference for the disclosure of the preparation of the plasmid): a 6 kb fragment (PacI/PmeI) and a 2.8 kb fragment (NcoI/EcoRV). The two coding region fragments and the two vector fragments were combined and transformed into PNY1500. Transformants were obtained via selection on synthetic complete medium lacking histidine. The resulting plasmid contained two gene cassettes-one expressing GMD from the PDC1 promoter (SEQ ID NO:32) with the ADH1 terminator (SEQ ID NO:33) and one expressing GMER from a hybrid promoter (PGK1(UAS)-FBA1) (SEQ ID NO:34) with the TDH3 terminator (SEQ ID NO:35). Correct plasmid clones were confirmed by sequencing. One plasmid was designated pRS413::GMD-GMER_Ec.

An additional plasmid expressing GMD and GMER enzymes from *Arabidopsis thaliana* was also prepared, essentially as described above. The gene sequences (SEQ ID NOs. 36 and 37) were obtained from IDT, cloned and sequenced as described above for the *E. coli* GMD/GMER pair and then transferred to the yeast expression vector using the same gap repair cloning strategy. The primers used to amplify the genes for this last step were H11 and H12 (GMD_At) and H13 and H14 (GMER_At), corresponding to SEQ ID NOs. 38-41. The host strain for the gap repair cloning was PNY1500 (above). Four clones identified by PCR were subsequently sequenced. One plasmid was designated pRS413::GMD-GMER_At. This plasmid was recovered from yeast cells (Zymo Prep™ Yeast Plasmid Miniprep 11 kit, Zymo Research, Cat. No. D2004) and propagated in *E. coli* Stbl3 cells (Invitrogen, Cat. No. C7373-03, transformed via the manufacturer's protocol). Plasmid DNA prepared from the transformed Stbl3 cells was used to transform yeast strain HS0003. Transformants were selected by plating the transformation mixture on synthetic complete medium without histidine. One clone was designated HS0004.

Construction of Plasmid Encoding □1,2-Fucosyltransferase

A nucleic acid molecule having the coding sequence for a fucosyltransferase (FutC) enzyme from *Helicobacter pylori* was obtained from a commercial gene synthesis company (IDT, Coralville, Iowa) (SEQ ID NO:42). The linear gene fragment was cloned into pCRII-Blunt™ (Zero Blunt™ TOPO™ cloning vector, Invitrogen™) per the manufacturer's instructions. Clones were sequenced using standard M13 forward and reverse primers. One clone was digested with BsaI and the futC coding region fragment was cloned into a pY-SUMOstar® plasmid (Life Sensors™, Malvern, Pa.) also previously cut with BsaI. Ligation mixtures were transformed into *E. coli* Stbl3 cells. Colonies arising with ampicillin selection (100 μg/mL) were screened by PCR to confirm the futC clones.

The pY-SUMOstar::futC_Hp plasmid was further modified to change the selectable marker from TRP1 to URA3. This was done by digesting the plasmid with Bsu36I and transforming the linear DNA fragment into HS0004 (above) along with a linear DNA fragment containing the URA3 selectable marker as amplified from pRS426 (ATCC #77107) using primers H305 and H306 (SEQ ID NOs. 43 and 44). Successfully transformed colonies were selected for on synthetic complete medium without uracil and histidine. Colonies were screened by PCR using primers H291 and H292 (SEQ ID NOs. 45 and 46). Three of these transformants were evaluated for production of 2'FL, as described in Example 2. The pY-SUMOstar-URA::futC_Hp plasmid was recovered from one clone (designated HS0006) using the Zymo Prep™ kit. Plasmids were transferred to *E. coli* Stbl3 cells (Invitrogen, catalog number C7373-03) per the manufacturer's instructions. Plasmids prepared from Stbl3 cells were used to transform HS0003 along with pRS413::GMD-GMER_Ec (strain and plasmid described above). Transformants again were evaluated as described in Example 2 and one 2'FL-producing clone was designated HS0007. Negative control strains were also prepared by transforming strain HS0003 with only the fucosyltransferase plasmid (plus empty plasmid pRS413) and transforming strain HS0004 with an empty URA3 selectable plasmid (pHR81, ATCC #87541).

Example 2

Measurement of 2'FL Production

Intracellular Measurement of 2'FL

Strains transformed with plasmids carrying 2'FL pathway genes (Example 1) were evaluated in shake flasks. Clones, e.g., HS0007 and siblings, were inoculated into synthetic complete medium without histidine, tryptophan and uracil and incubated at 30° C. with agitation (200 rpm, Infors™ Multitron platform shaker). Overnight cultures were adjusted to 0.1 to 0.2 OD (Eppendorf™ BioPhotometer®, Hamburg Germany) and grown to an OD of approximately 1. Lactose was added to 0.5% (w/v) and copper sulfate was added (100 μM) to increase the expression of FutC_Hp, which is under control of the CUP1 promoter. At various times post-induction, culture samples (ca. 2-10 mL) were centrifuged to separate cells from medium. The cell pellets were frozen at −80° C. Culture supernatants were filtered through 0.22 micron Costar® Spin-X® filter tubes (Corning™, Corning, N. Y.) or AcroPrep™ Advance 96 filter plates (Pall, Ann Arbor, Mich.) and stored at −20° C.

Cell pellets were thawed at room temperature just prior to use. An aliquot of 0.425 mL of 0.2 μm filtered NanoPure™ water was added to each thawed cell pellet, and the pellet was resuspended by pipetting up and down. The suspension was transferred to a 1.5 mL microcentrifuge tube. The sample was heated at 98° C. on a heat block (Eppendorf™) for six minutes, cooled briefly on ice, vortexed, and centrifuged at 10,000×g for 10 minutes. An aliquot of 40 μL of the resulting supernatant was added to a new microcentrifuge tube and diluted with the addition of 80 μL of acetonitrile. The 120 μL of acetonitrile-diluted supernatant was transferred to the top of a Nanosep® MF Centrifugal Device, 0.2 μm (Pall) which was then centrifuged at 10,000×g for one minute. The filtrate was added to a LC vial with a low volume insert.

Samples were analyzed by UHPLC-ELSD (Shimadzu™Nexera™ X2). The column used was an Acquity UHPLC BEH Amide 1.7 μm, 2.1×100 mm (Waters™) with a Waters™ guard column of the same material. The injection volume for each sample was 4 μL. Buffer A was 10% acetonitrile in water, and Buffer B was 100% acetonitrile. A gradient elution was run that involved an initial hold of 25% Buffer A for 2.3 min, followed by a gradient to 60% Buffer A at 6.5 min, followed by a gradient to 90% Buffer A at 7.00 min and a hold of this percentage to 7.5 min, and then a re-equilibration to 25% Buffer A to 10.0 min. Standard runs with D-(+)-glucose (Sigma-Aldrich™ G7528 Lot SLBK8673V), α-lactose monohydrate (Carbosynth™ OL050091401), 2'FL (Carbosynth™ OF067391403), and lactodifucotetraose (LDFT, Carbosynth™ OL065671201) resulted in retention times of 1.8 minutes, 3.3 minutes, 4.4 minutes, and 5.4 minutes respectively. Calibration curves were run for these components and were used to produce raw concentration data. OD600 values and the sample amounts were used to normalize the intracellular concentrations as follows:

Normalized mM=(Raw mM)*(0.425 mL+

(OD*V centrifuged*0.0009594 mL OD$^{-1}$))/(OD*V centrifuged*0.0009594 mL OD$^{-1}$).

The 0.0009594 mL/OD factor was estimated based on a haploid cell volume (Sherman. "Getting started with yeast", Methods in Enzymology (2002) 350:3-41). Alternatively, data may be normalized to the cell culture volume from which the cells were harvested for comparison to extracellular concentrations. The results are shown in Table 1, below.

TABLE 1

Intracellular 2'FL measurements from shake flask-cultured cells. 2'FL was extracted from cell pellets and measured as described in Example 2. Sampling time was 16 hours after addition of lactose (0.5% w/v) and copper sulfate (0.1 mM).

| Strain Designation (if applicable) | Base Strain/plasmids | 2'FL normalized to intracellular concentration, mM |
|---|---|---|
|  | HS0003/pY-SUMOstar-URA::futC_Hp/pRS413 (3 clones) | Not detected |
|  | HS0003/pHR81/pRS413::GMD-GMER_At (3 clones) | Not detected |
| HS0006 | HS0003/pY-SUMOstar-URA::futC_Hp/pRS413::GMD-GMER_At | 59.5 ± 0.3 (n = 2) |
|  | HS0003/pY-SUMOstar-URA::futC_Hp/pRS413::GMD-GMER_Ec Clone #1 | 101 |
|  | HS0003/pY-SUMOstar-URA::futC_Hp/pRS413::GMD-GMER_Ec Clone #2 | 118 |
| HS0007 | HS0003/pY-SUMOstar-URA::futC_Hp/pRS413::GMD-GMER_Ec Clone #3 | 107 |

Extracellular Detection of 2'FL

Extracellular 2'-fucosyl lactose was measured with an enzyme based fluorometric assay. Yeast culture supernatants were filtered using Spin-X® 0.22 μM Nylon tube filters and 100 μl of filtrates were diluted two fold into 202 mM sodium phosphate pH 6, containing 1.51 units of *T. maritima* fucosidase (E-FUC™, Megazyme™ International Ireland). The mixtures were incubated at 90° C. for 10 minutes. The amounts of fucose in the resultant solutions were measured with the L-fucose assay kit (K-Fucose, Megazyme™ International Ireland), based on fucose dehydrogenase catalyzed oxidation of fucose with concomitant reduction of NADP. 26.2 μl of fucosidase treated samples were diluted 10 fold in the fucose dehydrogenase reaction mixture, prepared according to the vendor. The solutions were incubated for 19 min at 37° C. NADPH fluorescence was then measured in a Wallac 1420 Victor3™ Microplate Reader (Perkin Elmer), employing a 355 nm cut-off filter for excitation and 450 nm filter for emission. A fucose standard was employed to calculate fucose formed in each reaction. Samples with and without fucosidase were compared to specifically quantitate the amounts of fucose generated during the fucosidase treatment step, providing extracellular 2'fucosyllactose concentrations in the supernatants.

Example 3

Intracellular and Extracellular Concentrations of 2'FL Under Various Growth Conditions Glucose Excess Versus Glucose Limited Inoculum Preparation A frozen vial of HS0007 (prepared as described in Example 1) was thawed and transferred to 10 mL synthetic complete medium with 2% glucose in a 125 mL vented shake flask, and incubated at 30° C. and 300 rpm shaking for several hours. Two seed flasks were prepared using this culture in two 250 mL vented shake flasks with 40 mL of synthetic complete medium with 2% glucose for further growth at 30° C. and 300 rpm shaking. When the culture reached OD600 about 4, the two flask cultures were used to inoculate two 1 L fermenters. The synthetic complete medium composition is as follows: yeast nitrogen base without amino acids (Difco), 6.7 g/L; Synthetic Complete Drop-out:(Kaiser)-his-ura (Formedium, England), 1.8 g/L; glucose was added to 2% (w/v) for the inoculum growth. The pH was adjusted to 5.2 with 20% potassium hydroxide and the medium filter sterilized through a 0.22μ filter.

Fermenter Preparation and Operation:

Fermentations were carried out in 1 L Biostat® B DCU3 fermenters (Sartorius, USA). Two fermenters were prepared with 500 mL 0.9% (w/v) NaCl solution and sterilized at 121' C for 30 minutes. After cooling, the salt solution was pushed out and 760 mLs medium, which had been previously filter sterilized, was pumped into the fermenters. Synthetic complete medium with 0.2 mL antifoam (DF204, Sigma, USA) was used in both fermentations; the medium for one fermenter (V1) was prepared with 2% glucose and for the second fermenter (V2) with 0.1% glucose. The temperature of the fermenter was maintained at 30° C., and pH controlled at 5.5 with 20% KOH throughout the entire fermentations. Aeration was controlled at 0.4 standard liters per minute, and dissolved oxygen controlled at 20% by agitation. Samples were drawn and analyzed for optical density at 600 nm and for glucose concentration by a YSI™ Select Biochemistry Analyzer (YSI™, Inc., Yellow Springs, Ohio). Glucose excess was maintained throughout the fermentation in V1, at 5-30 g/L by manual additions of a 50% (w/w) solution. Fermenter V2 was run with glucose limitation using a programmed exponential ramp feed of 50% (w/w) glucose controlled with an exponential ramp of 0.12/hr. The glucose feed was delivered via syringe pumps (KD Scientific, Inc., USA). When glucose measurements in Fermenter V2 exceeded 0.1 g/L, the feed rate was slowed to bring it back to the limited condition. When the optical density was about 1.5, CuSO4 to a final concentration of 100 µM and lactose to a final concentration of 5 g./L were added to each fermenter.

Figure 2A:
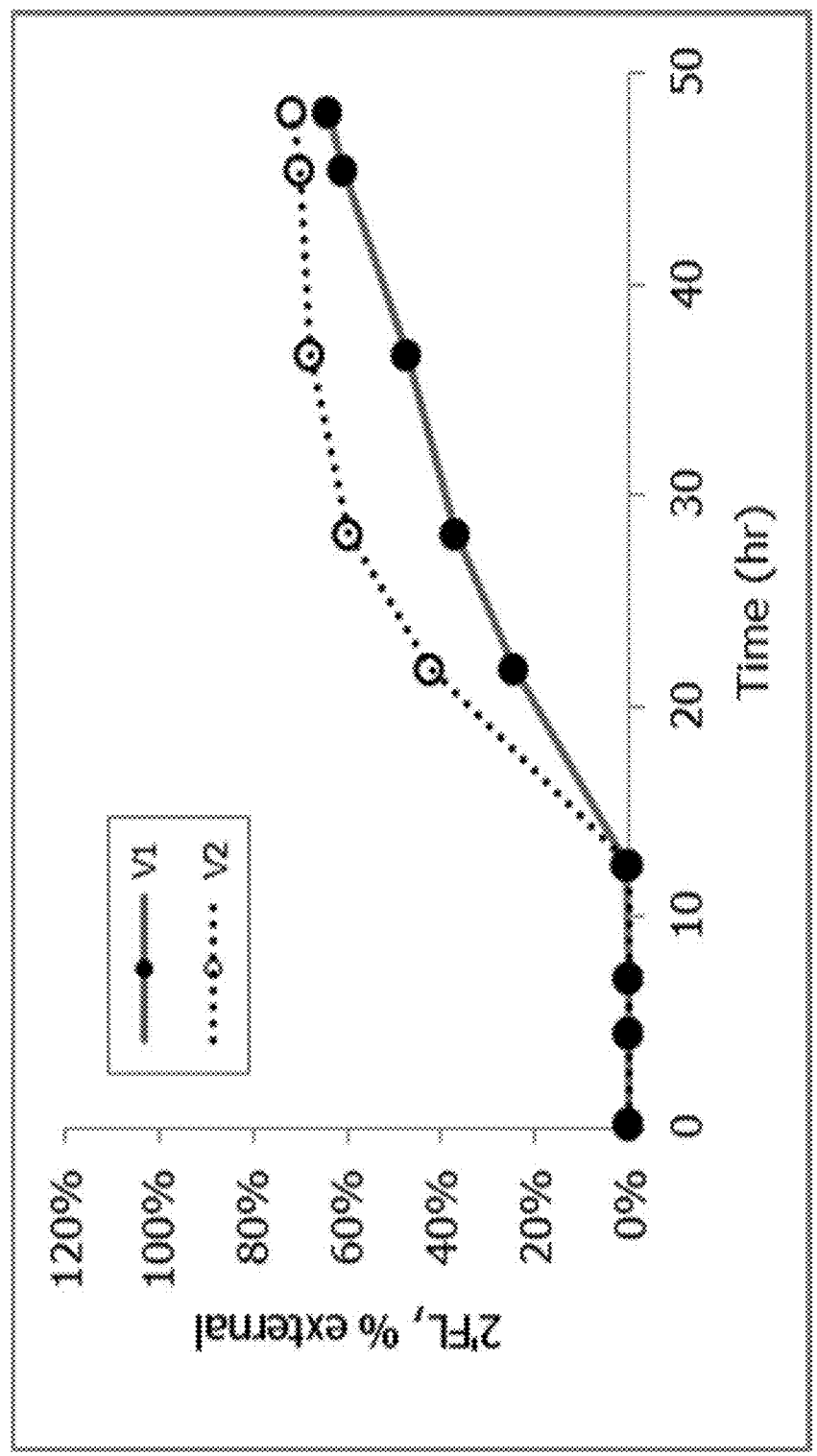
FIG. 2 (A-C) shows a comparison of 2' fucosyllactose export from yeast cells in glucose excess versus glucose limited growth conditions.
Figure 2B:
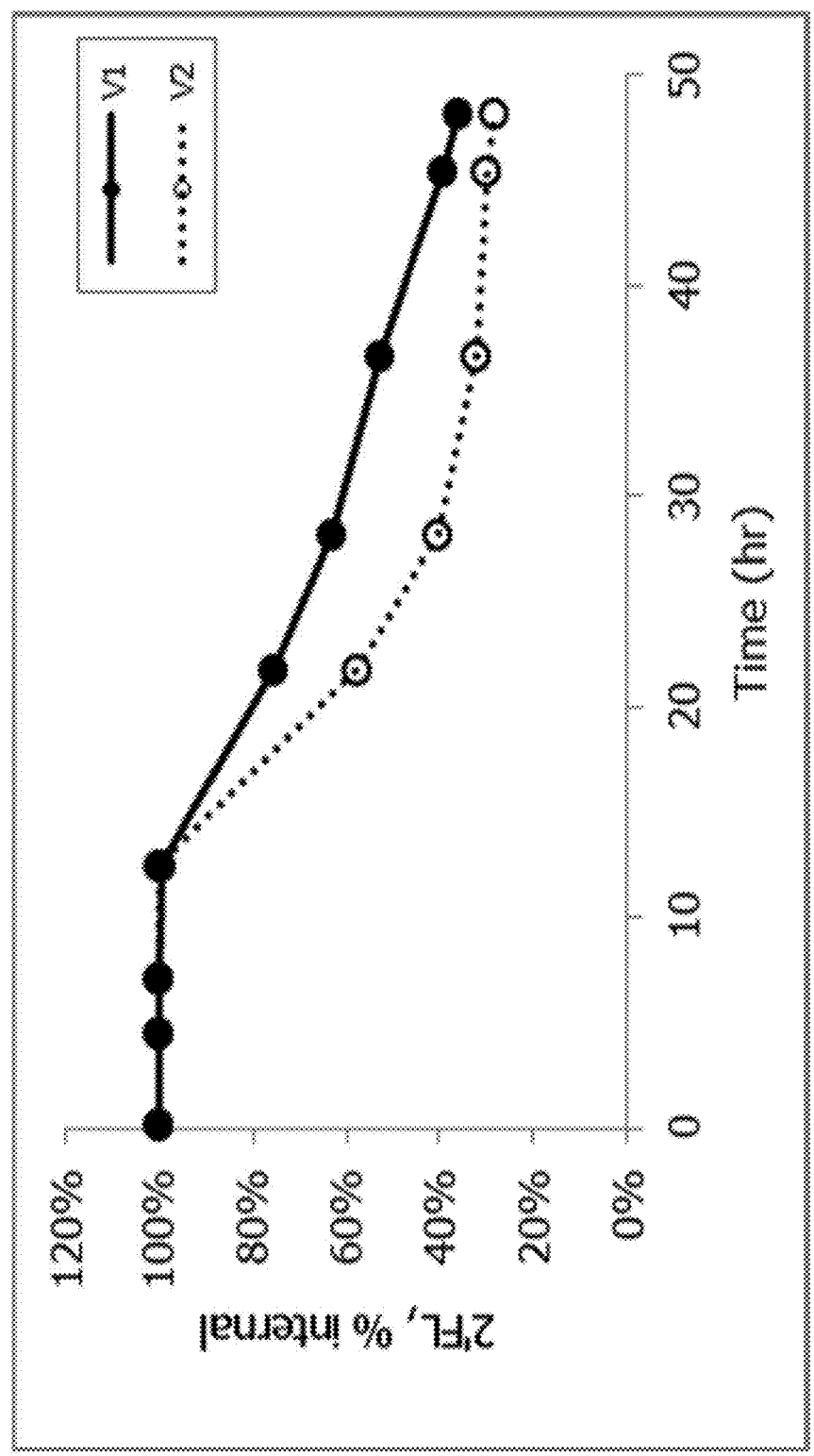
Figure 2C:
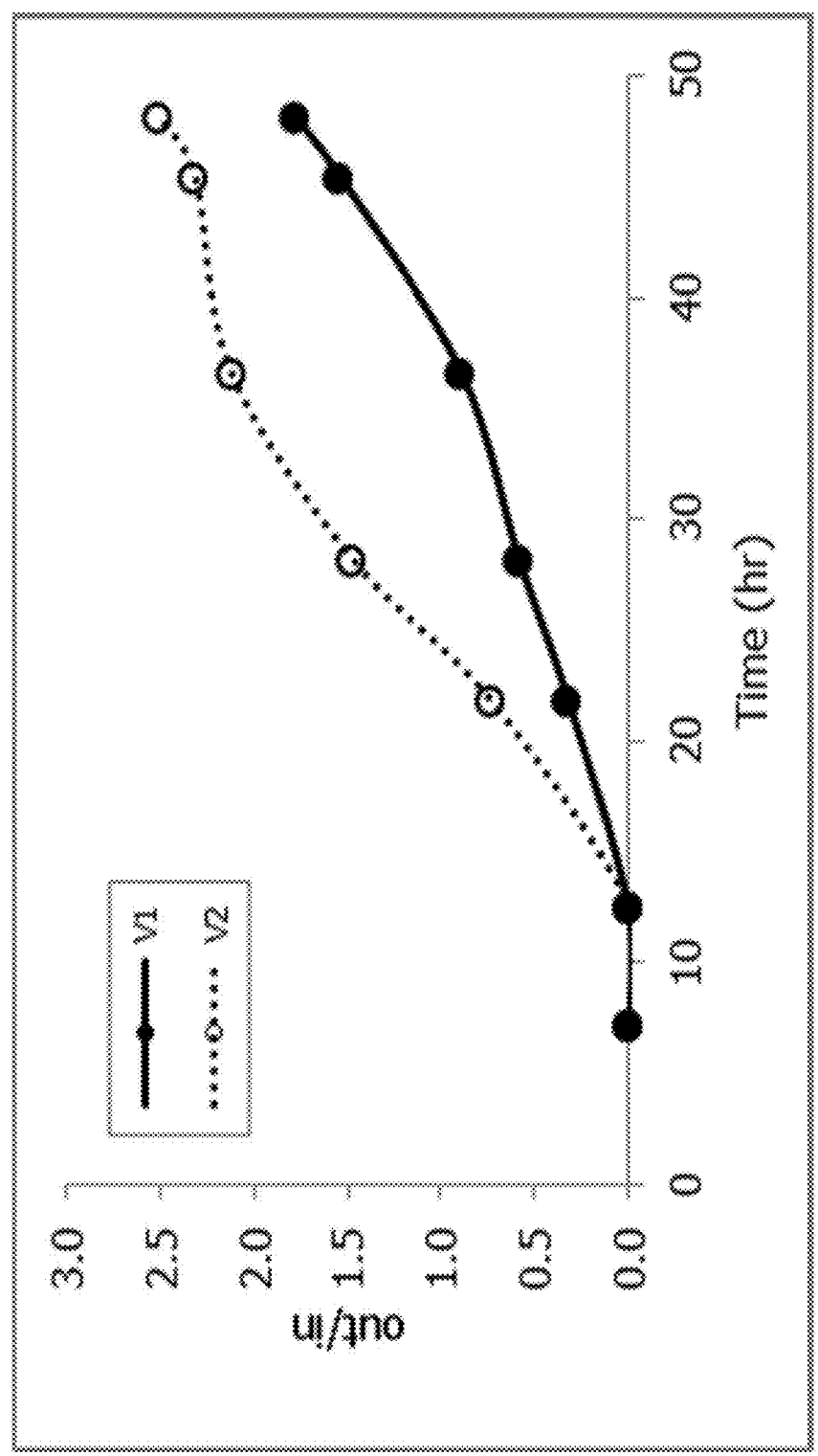

Samples from both fermenters were centrifuged to separate the biomass and cell pellets. Both fractions were stored at −80 C until analysis at the end of the experiment. Intracellular and extracellular 2'FL amounts from the cell pellets were determined as described in Example 2. The results in terms of extracellular and intracellular 2'FL percentages and the extracellular to intracellular 2'FL ratio are shown in FIGS. 2A-2C, respectively. As shown in FIGS. 2A-2C, in cells grown in glucose-limited conditions, a greater amount (percentage and ratio) of the 2'FL was found in the extracellular fraction.

Glucose Versus Ethanol as a Carbon Source
Inoculum Preparation

A frozen vial of HS0007 (prepared as described in Example 1) was thawed and transferred to 10 mL synthetic complete medium with 2% glucose in a 125 mL vented shake flask, and incubated at 30° C. and 300 rpm shaking for several hours. Two seed flasks were prepared using this culture in two 250 mL vented shake flasks with 40 mL of synthetic complete medium with 2% glucose for further growth at 30° C. and 300 rpm shaking. When the culture reached OD600 about 4, the two flask cultures were used to inoculate two 1 L fermenters. The synthetic complete medium composition is as follows: yeast nitrogen base without amino acids (Difco™), 6.7 g/L; Synthetic Complete Drop-out:(Kaiser™) -his -ura (Formedium, England), 1.8 g/L; glucose was added to 2% (w/v) for the inoculum growth. The pH was adjusted to 5.2 with 20% potassium hydroxide and the medium filter sterilized through a 0.22µ filter.

Fermenter Preparation and Operation:

Fermentations were carried out in 1 L Biostat® B DCU3 fermenters (Sartorius™, USA). Two fermenters were prepared with 500 mL 0.9% (w/v) NaCl solution and sterilized at 121' C for 30 minutes. After cooling, the salt solution was pushed out and 760 mLs medium, which had been previously filter sterilized, was pumped into the fermenters. Synthetic complete medium with 0.2 mL antifoam (DF204, Sigma™, USA) was used in both fermentations; the medium for one fermenter (V1) was prepared with 2% glucose and for the second fermenter (V2) with 2% ethanol. The temperature of the fermenter was maintained at 30° C., and pH controlled at 5.5 with 20% KOH throughout the entire fermentations. Aeration was controlled at 0.4 standard liters per minute, and dissolved oxygen controlled at 20% by agitation. Samples were drawn and analyzed for optical density at 600 nm and for glucose concentration by a YSI™ Select Biochemistry Analyzer (YSI™, Inc., Yellow Springs, Ohio). Glucose excess was maintained throughout the fermentation in V1, at 5-30 g/L by manual additions of a 50% (w/w) solution. Fermenter V2 was fed ethanol back to 20 g/L at 25 hours elapsed fermentation time. When the optical density was about 1.5, CuSO4 to a final concentration of 100 µM and lactose to a final concentration of 5 g./L were added to each fermenter.

Figure 3A:
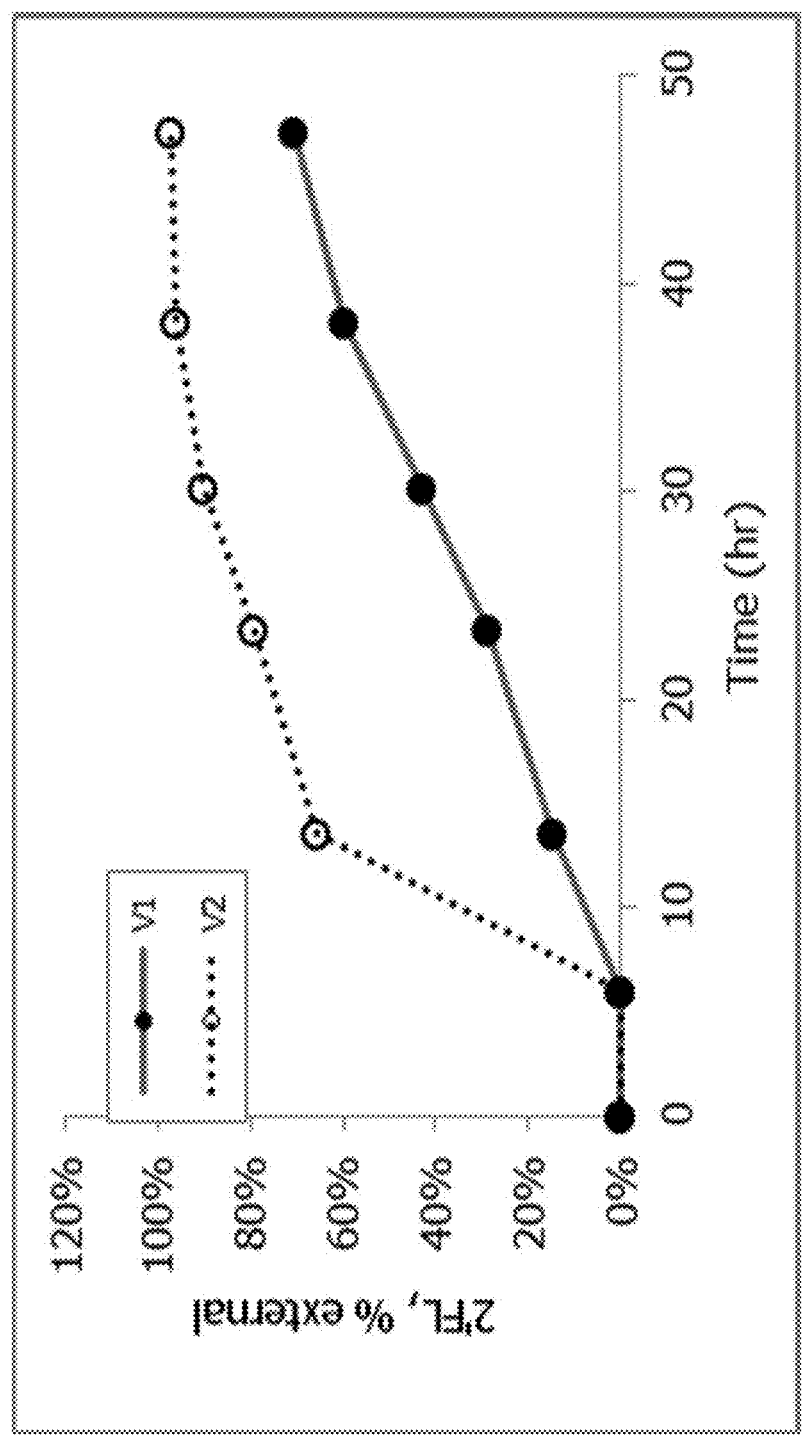
FIG. 3 (A-C) shows a comparison of 2' fucosyllactose export from yeast cells grown in media supplemented with glucose or ethanol.
Figure 3B:
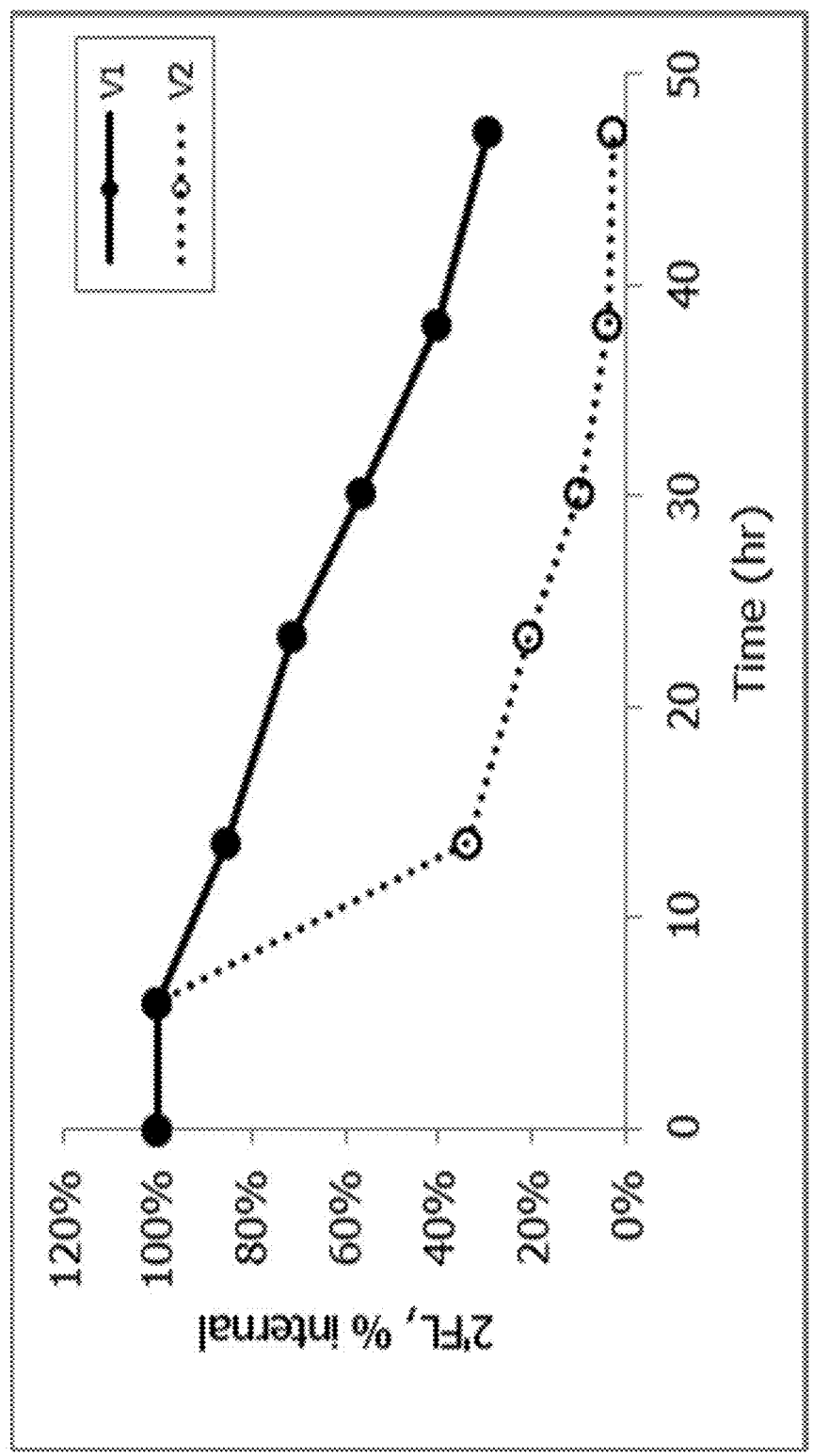
Figure 3C:
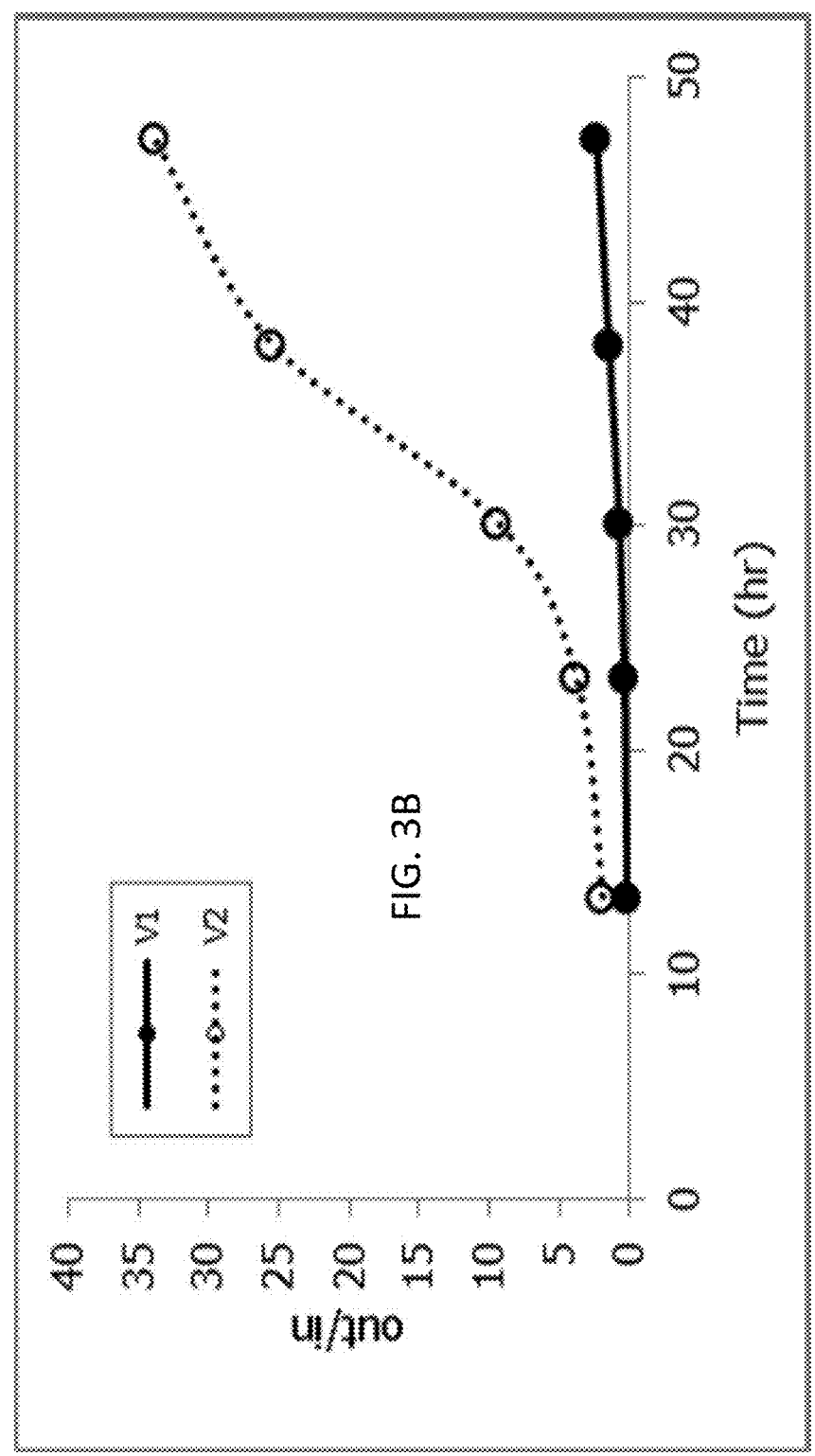

Samples from both fermenters were centrifuged to separate the biomass and cell pellets. Both fractions were stored at −80 C until analysis at the end of the experiment. Intracellular and extracellular 2'FL amounts from the cell pellets were determined as described in Example 2. The results in terms of extracellular and intracellular 2'FL percentages and the extracellular to intracellular 2'FL ratio are shown in FIGS. 3A-3C, respectively. As shown in FIGS. 3A-3C, in cells grown in the presence of ethanol, a greater amount (percentage and ratio) of the 2'FL was found in the extracellular fraction.

Synthetic Versus Defined Medium
Inoculum Preparation

A frozen vial of HS0007 (prepared as described in Example 1) was thawed and transferred to 10 mL synthetic complete medium with 2% glucose in a 125 mL vented shake flask, and incubated at 30° C. and 300 rpm shaking for several hours. Two seed flasks were prepared using this culture in two 250 mL vented shake flasks with 40 mL of synthetic complete medium with 2% glucose for further growth at 30° C. and 300 rpm shaking. When the culture reached OD600 about 4, the two flask cultures were used to inoculate two 1 L fermenters. The synthetic complete medium composition is as follows: yeast nitrogen base without amino acids (Difco™), 6.7 g/L; Synthetic Complete Drop-out:(Kaiser™) -his -ura (Formedium, England), 1.8 g/L; glucose was added to 2% (w/v) for the inoculum growth. The pH was adjusted to 5.2 with 20% potassium hydroxide and the medium filter sterilized through a 0.22µ filter.

Fermenter Preparation and Operation:

Fermentations were carried out in 1 L Biostat B DCU3 fermenters (Sartorius, USA). Two fermenters were prepared with 500 mL 0.9% (w/v) NaCl solution and sterilized at 121'C for 30 minutes. After cooling, the salt solution was pushed out and 760 mLs medium, which had been previously filter sterilized, was pumped into the fermenters. Synthetic complete medium with 2% glucose and 0.2 mL antifoam (DF204, Sigma, USA) was used in fermenter V1. The second fermenter. V2, was prepared with a minimal medium with the following composition, per liter: 5 g ammonium sulfate, 6 g potassium phosphate monobasic, 2 g magnesium sulfate heptahydrate, 1 mL of a trace mineral solution (prepared in 1 L water: 15 g EDTA, 4.5 g zinc sulfate heptahydrate, 0.8 g manganese chloride dehydrate, 0.3 g cobalt chloride hexahydrate, 0.3 g copper sulfate pentahydrate, 0.4 g disodium molybdenum dehydrate, 4.5 g calcium chloride dihydrate, 3 g iron sulfate heptahydrate, 1 g boric acid, 0.1 g potassium iodide) and 1 mL of a vitamin mixture (in 1 L water, 50 mg biotin, 1 g Ca-pantothenate, 1 g nicotinic acid, 25 g myo-inositol, 1 g pyridoxol hydrochloride, 0.2 g p-aminobenzoic acid), 20 g glucose and 0.2 mL Sigma Antifoam 204.

The temperature of the fermenters was maintained at 30° C., and pH controlled at 5.5 with 20% KOH throughout the entire fermentations. Aeration was controlled at 0.4 standard liters per minute, and dissolved oxygen controlled at 20% by agitation. Samples were drawn and analyzed for optical density at 600 nm and for glucose concentration by a YSI™ Select Biochemistry Analyzer (YSI™, Inc., Yellow Springs, Ohio). Glucose excess was maintained throughout both fermentations, at 5-30 g/L, by manual additions of a 50% (w/w) solution. When the optical density was about 1.5, CuSO4 to a final concentration of 100 µM and lactose to a final concentration of 5 g./L were added to each fermenter.

Figure 4A:
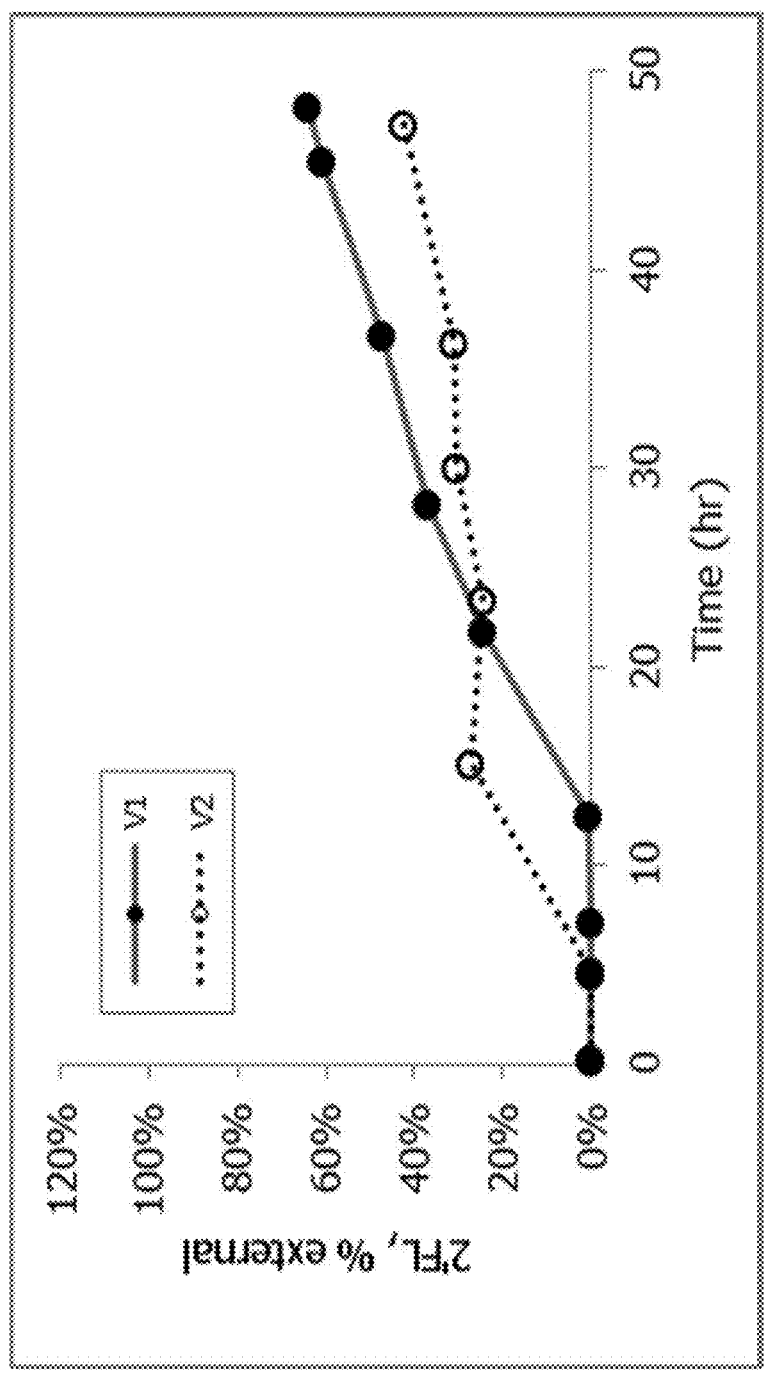
FIG. 4 (A-C) shows a comparison of 2' fucosyllactose export from yeast cells grown in synthetic complete versus minimal media.
Figure 4B:
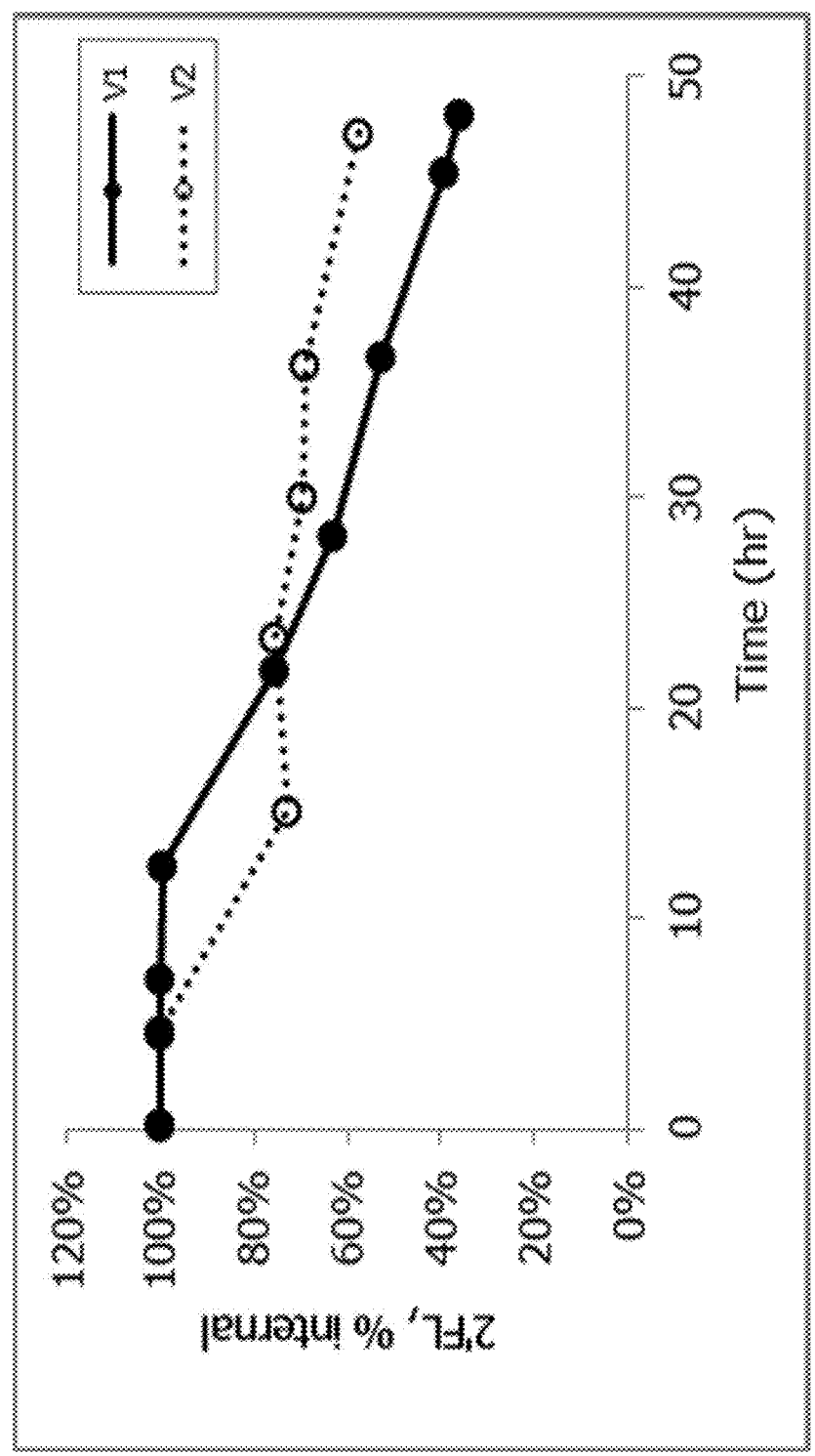
Figure 4C:
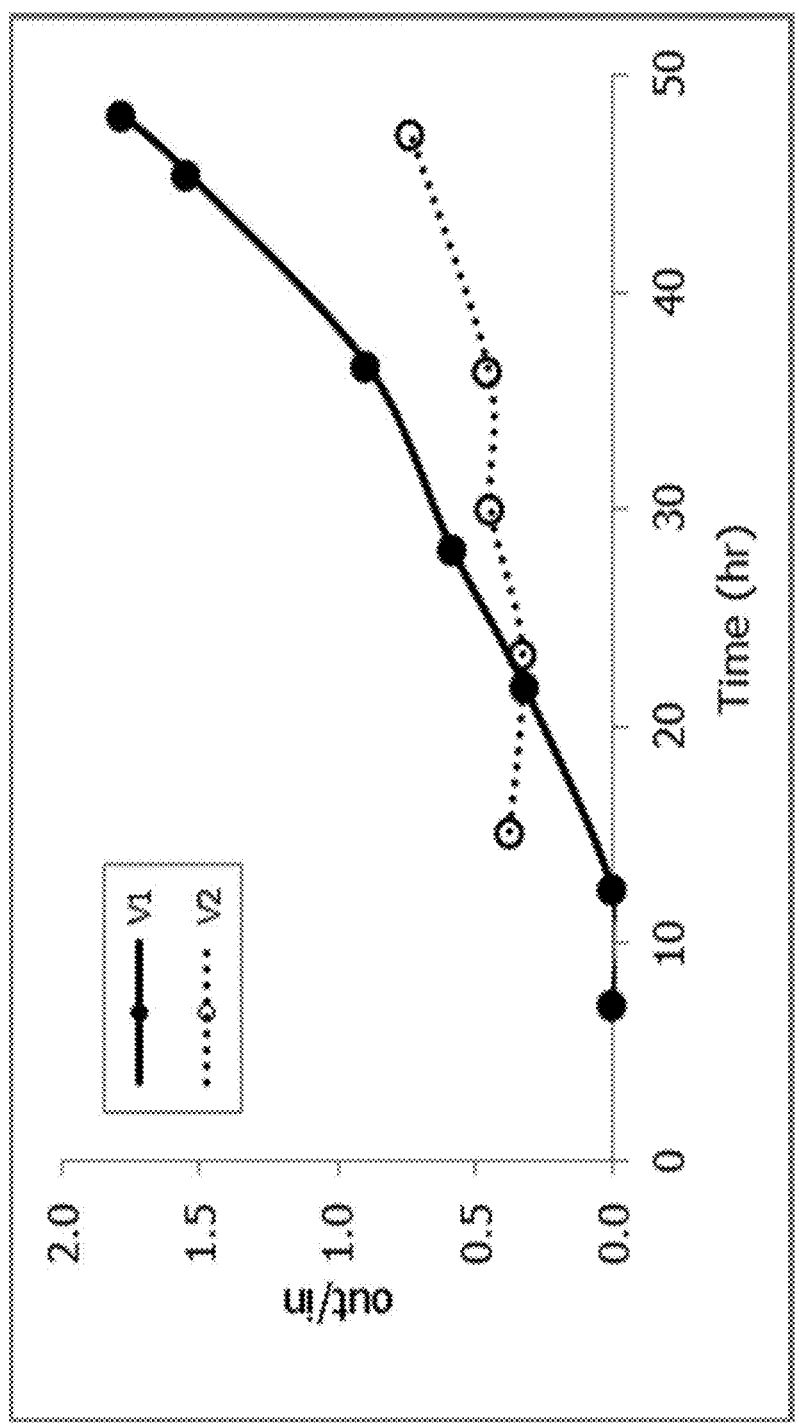

Samples from both fermenters were centrifuged to separate the biomass and cell pellets. Both fractions were stored at −80 C until analysis at the end of the experiment. Intracellular and extracellular 2'FL amounts from the cell pellets were determined as described in Example 2. The results in terms of extracellular and intracellular 2'FL percentages and the extracellular to intracellular 2'FL ratio are shown in FIGS. 4A-4C, respectively. As shown in FIGS. 4A-4C, in cells grown in the presence of synthetic complete medium, a greater amount (percentage and ratio) of the 2'FL was found in the extracellular fraction.

Example 4

Identification of Endogenous Transporters for 2'FL

The following example discloses a method to identify 2'FL transporters endogenous to microbial cells.

Samples are taken over the course of the fermentations described in Example 3 for transcriptome analysis. A 1 mL sample is taken directly from the fermenter and centrifuged for 2 minutes. After removal of the supernatant, 1 mL of Trizol® Reagent (Life Technologies™, USA) is added to the tube, the pellet resuspended, and samples stored at −80 C until analysis. The samples are processed to recover RNA submitted for RNASeq analysis. Potential candidates for endogenous transporters are identified by comparison of the transcript profile of cells grown in the fermentation conditions described in Example 3. Genes that are more highly expressed in cells grown in each of the respective comparative conditions where increased 2'FL export was seen (e.g., ethanol versus glucose as the carbon source) are further analyzed to select those genes that are both more highly expressed and that are either annotated as coding for transporters or are homologous to known transporters. The selected candidates are then evaluated by knocking out the gene and by overexpressing the gene in yeast by a constitutive promoter. The yeast cells containing knockouts and overexpressing the candidate transporters are then assayed for loss and gain of 2'FL export function, respectively.

What is claimed is:

1. A fermentation broth comprising a 2' fucosyllactose-producing microbial cell having increased export of 2' fucosyllactose, the microbial cell having been subjected to a condition,
  wherein the microbial cell having been subjected to the condition exhibits decreased levels of intracellular 2' fucosyllactose compared to levels of intracellular 2' fucosyllactose in the microbial cell in the absence of subjecting the microbial cell to the condition,
  wherein the condition comprises at least one of
    growing the microbial cell in a medium comprising amino acids in comparison to growing the microbial cell in a medium without amino acids,
    growing the microbial cell in a glucose limited medium comprising at least 0.1% glucose (w/v) in comparison to growing the microbial cell in a medium having glucose excess, and growing the microbial cell in a medium comprising ethanol as a carbon source for the microbial cell in comparison to growing the microbial cell in a medium comprising glucose as the carbon source for the microbial cell.

2. The fermentation broth of claim 1, wherein the microbial cell is a yeast cell.

3. A fermentation broth comprising:

a yeast cell that produces and exports 2' fucosyllactose, wherein the yeast cell has been subjected to a condition that results in decreased levels of intracellular 2' fucosyllactose in comparison to levels of intracellular 2' fucosyllactose in a yeast cell not subjected to the condition, and wherein the condition comprises at least one of growing the yeast cell in a medium comprising amino acids in comparison to growing the yeast cell in a medium without amino acids, and growing the yeast cell in a glucose limited medium comprising at least 0.1% glucose (w/v) in comparison to growing the yeast cell in a medium having glucose excess, growing the yeast cell in a medium comprising ethanol as a carbon source for the yeast cell in comparison to growing the yeast cell in a medium comprising glucose as the carbon source for the microbial cell.

* * * * *

UNITED STATES PATENT AND TRADEMARK OFFICE
CERTIFICATE OF CORRECTION

| | |
|---|---|
| PATENT NO. | : 12,071,614 B2 |
| APPLICATION NO. | : 17/049855 |
| DATED | : August 27, 2024 |
| INVENTOR(S) | : Lisa A. Laffend, Mark J. Nelson and Lori Ann Maggio-Hall |

It is certified that error appears in the above-identified patent and that said Letters Patent is hereby corrected as shown below:

In the Specification

| | | |
|---|---|---|
| Column 1, | Lines 27-28, | change "of an □-1,2-fucosyltransferase to" to --of an α-1,2-fucosyltransferase to-- |
| Column 2, | Line 18, | change "production of 2-FL." to --production of 2′FL.-- |
| Column 2, | Line 50, | change "pUC19-URA3-YPRCA15." to --pUC19-URA3-YPRCΔ15.-- |
| Column 3, | Line 22, | change "terms "comprises." "comprising," to --terms "comprises," "comprising,"-- |
| Column 3, | Line 23, | change ""has," "having." "contains" or" to --"has," "having," "contains" or-- |
| Column 3, | Lines 55-56, | change "these procedures: through" to --these procedures; through-- |
| Column 5, | Line 50, | change "NY (1984): and" to --NY (1984); and-- |
| Column 5, | Line 52, | change "Current Protocols. John Wiley" to --Current Protocols, John Wiley-- |
| Column 7, | Line 12, | change "12, 40-53: US" to --12, 40-53; US-- |
| Column 7, | Lines 14-15, | change "*Saccharomyces, Yarrowia Kluyveromyces*," to --*Saccharomyces, Yarrowia, Kluyveromyces*,-- |
| Column 7, | Line 23, | change "and 2-N-L-fucosyltransferase" to --and 2-α-L-fucosyltransferase-- |
| Column 8, | Line 38, | change "with an □-1,2-L-fucosidase" to --with an α-1,2-L-fucosidase-- |
| Column 8, | Line 40, | change "with an NAD*-dependent" to --with an NAD+-dependent-- |
| Column 8, | Line 44, | change "which moves H+ during" to --which moves $H^+$ during-- |
| Column 11, | Line 8, | change "liter(s). "ml"" to --liter(s), "ml"-- |
| Column 11, | Line 9, | change "milliliter(s), "□L" means" to --milliliter(s), "μL" means"-- |
| Column 11, | Line 10, | change ""□g" means" to --"μg" means-- |
| Column 11, | Line 11, | change "millimolar, "□M" means" to --millimolar, "μM" means-- |
| Column 11, | Line 12, | change "micromolar. "nm" means" to --micromolar, "nm" means-- |

Signed and Sealed this
Nineteenth Day of November, 2024

*Katherine Kelly Vidal*

Katherine Kelly Vidal
*Director of the United States Patent and Trademark Office*

Page 1 of 2

CERTIFICATE OF CORRECTION (continued)
U.S. Pat. No. 12,071,614 B2

| Column 11, | Line 12, | change "nanometer(s), "☐mol" means" to --nanometer(s), μmol means-- |
| --- | --- | --- |
| Column 11, | Line 13, | change "means picomole(s)," to --means picomole(s).-- |
| Column 11, | Line 18, | change "Laboratory: Cold Spring" to --Laboratory, Cold Spring-- |
| Column 11, | Line 21, | change "Laboratory: Cold Spring" to --Laboratory, Cold Spring-- |
| Column 11, | Line 26, | change "Harbor, NY" to --Harbor, NY.-- |
| Column 11, | Line 43, | change "resin Chelex® resin (BioRad," to --resin Chelex® (BioRad,-- |
| Column 11, | Line 56, | change "Permease GeneA nucleic" to --Permease Gene A nucleic-- |
| Column 12, | Line 45, | change "(IDT, Coralville, Iowa)." to --(IDT™, Coralville, Iowa).-- |
| Column 13, | Line 36, | change "obtained from IDT," to --obtained from IDT™,-- |
| Column 13, | Line 47, | change "Miniprep 11 kit," to --Miniprep II kit,-- |
| Column 13, | Line 47, | change "Zymo Research" to --Zymo™ Research-- |
| Column 13, | Line 48, | change "(Invitrogen, Cat. No." to --(Invitrogen™, Cat. No.-- |
| Column 13, | Line 55, | change "Plasmid Encoding ☐1,2-fucosyltransferase" to --Plasmid Encoding α1,2-fucosyltransferase-- |
| Column 13, | Line 59, | change "company (IDT," to --company (IDT™,-- |
| Column 15, | Line 29, | change "(Sherman. "Getting started" to --(Sherman, "Getting started-- |
| Column 16, | Lines 22-23, | change "Excess Versus Glucose Limited Inoculum Preparation" to --Excess Versus Glucose Limited Inoculum Preparation:-- |
| Column 16, | Lines 44-45, | change "sterilized at 121'C for" to --sterilized at 121° C. for-- |
| Column 17, | Line 6, | change "at -80 C until analysis" to --at -80° C. until analysis-- |
| Column 17, | Line 39, | change "at 121'C for 30 minutes." to --at 121° C. for 30 minutes.-- |
| Column 17, | Line 62, | change "at -80 C until analysis" to --at -80° C. until analysis-- |
| Column 18, | Lines 27-28, | change "sterilized at 121'C for" to --sterilized at 121° C. for-- |
| Column 18, | Line 33, | change "second fermenter. V2, was" to --second fermenter, V2, was-- |
| Column 18, | Line 61, | change "at -80 C until analysis" to --at -80° C. until analysis-- |
| Column 19, | Lines 14-15, | change "at -80 C until analysis." to --at -80° C. until analysis-- |